(12) United States Patent
Morioka et al.

(10) Patent No.: US 9,387,155 B2
(45) Date of Patent: Jul. 12, 2016

(54) TABLET-INSPECTING DEVICE

(71) Applicant: Panasonic Corporation, Osaka (JP)

(72) Inventors: Junichiro Morioka, Mie (JP); Hiroshi Ehara, Ehime (JP); Toshiaki Ueta, Ehime (JP); Yoichi Oki, Ehime (JP); Akiji Tanaka, Ehime (JP); Shinichi Yasui, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 625 days.

(21) Appl. No.: 13/919,330

(22) Filed: Jun. 17, 2013

(65) Prior Publication Data

US 2013/0282159 A1 Oct. 24, 2013

Related U.S. Application Data

(63) Continuation of application No. PCT/JP2011/007048, filed on Dec. 16, 2011.

(30) Foreign Application Priority Data

| Dec. 17, 2010 | (JP) | ................................ 2010-281595 |
| Dec. 17, 2010 | (JP) | ................................ 2010-281605 |
| Dec. 17, 2010 | (JP) | ................................ 2010-281606 |
| Feb. 7, 2011 | (JP) | ................................ 2011-023609 |
| Feb. 7, 2011 | (JP) | ................................ 2011-023610 |
| Jul. 22, 2011 | (JP) | ................................ 2011-160585 |
| Oct. 26, 2011 | (JP) | ................................ 2011-234885 |

(51) Int. Cl.
| *G06F 7/00* | (2006.01) |
| *A61J 7/02* | (2006.01) |
| *G01N 21/95* | (2006.01) |
| *G05B 15/02* | (2006.01) |

(52) U.S. Cl.
CPC ............... *A61J 7/02* (2013.01); *G01N 21/9508* (2013.01); *G05B 15/02* (2013.01)

(58) Field of Classification Search
None
See application file for complete search history.

(56) References Cited

U.S. PATENT DOCUMENTS

| 2007/0150092 | A1 | 6/2007 | Ohmura et al. |
| 2010/0085428 | A1* | 4/2010 | Kim ........................ G01B 11/24 348/130 |
| 2012/0096807 | A1 | 4/2012 | Okuma |

FOREIGN PATENT DOCUMENTS

| JP | 2004-236997 A | 8/2004 |
| JP | 2004-238066 A | 8/2004 |
| JP | 2006-69618 A | 3/2006 |
| JP | 2012-440 A | 1/2012 |
| JP | 2012-85848 A | 5/2012 |
| WO | WO 2008/029606 A1 | 3/2008 |
| WO | WO 2010/041751 A1 | 4/2010 |

OTHER PUBLICATIONS

International Search Report for PCT/JP2011/007048, Mar. 19, 2012.

* cited by examiner

*Primary Examiner* — Yolanda Cumbess
(74) *Attorney, Agent, or Firm* — RatnerPrestia

(57) ABSTRACT

The present invention provides a tablet-inspecting device in which the control unit gives, to the continuous drug packet-driving unit, operation instructions to move the continuous drug packet from an upstream side to a downstream side of the conveyor path, and reciprocating operation instructions to alternately move the continuous drug packet to the upstream side and the downstream side of the conveyor path, the control unit gives, to the rod control unit, rod unit pressing operation instructions to press the rod unit against the side portion of the drug packet, and when the control unit gives the reciprocating operation instructions, the rod unit pressing operation instructions has been given, it is possible to enhance determining precision of the number of tablets or the kinds of tablet, and to stably inspect drugs.

23 Claims, 25 Drawing Sheets

Fig. 3
(a)
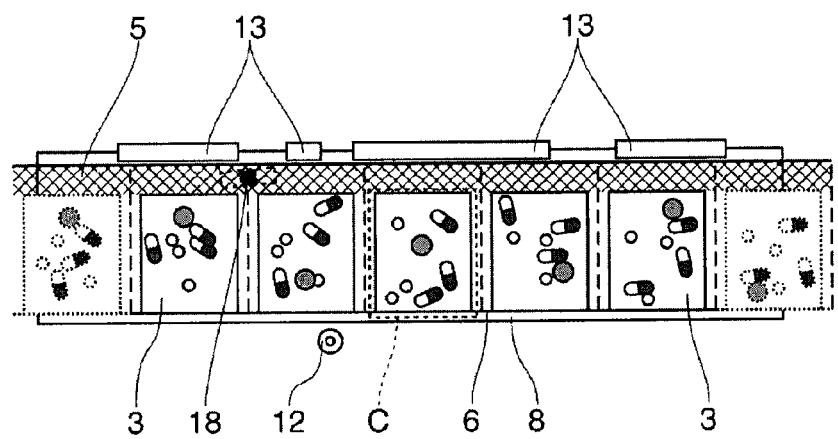
(b)
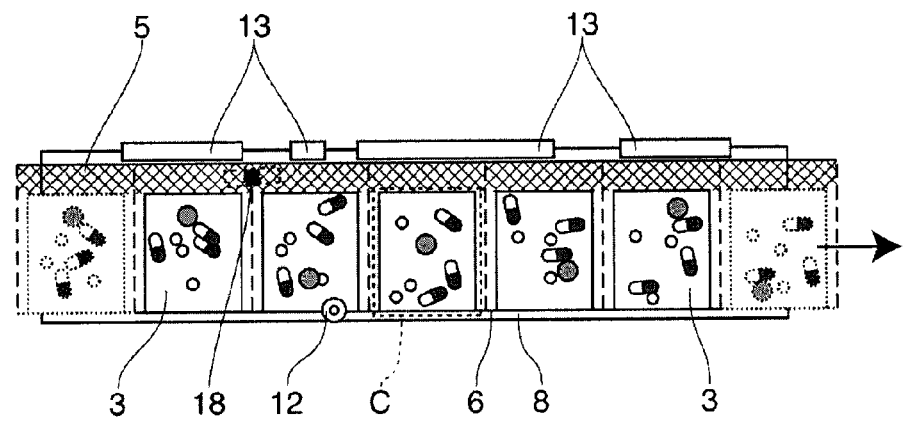

Fig. 4
(a)
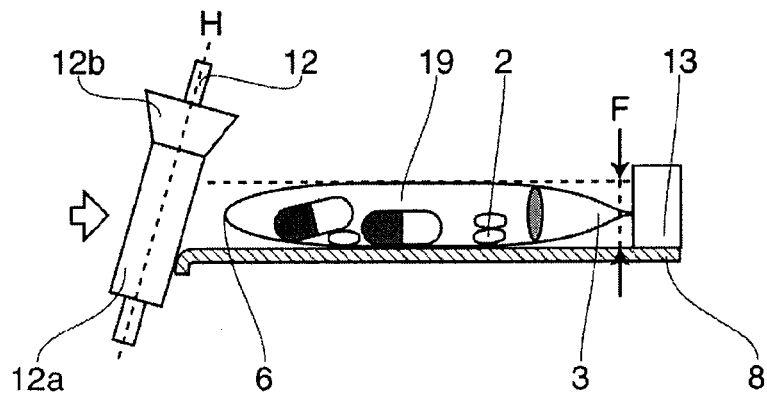
(b)
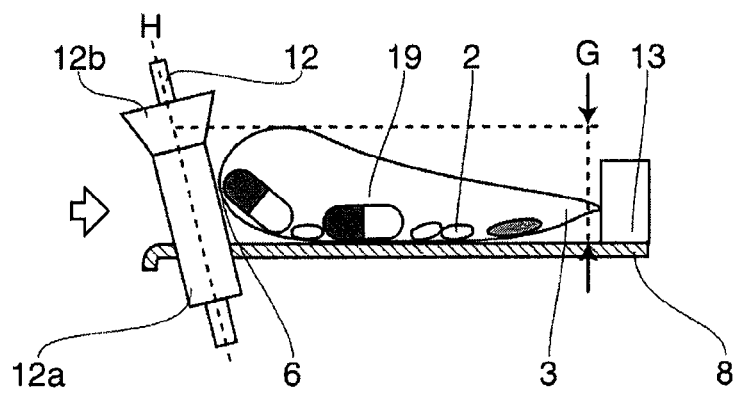
(c)
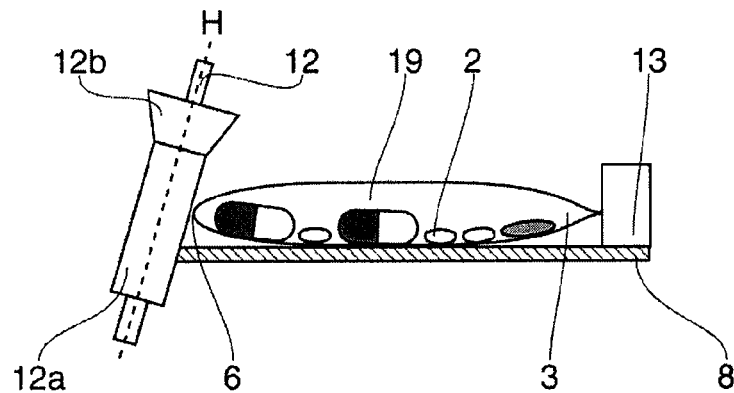

Fig. 5
(a)
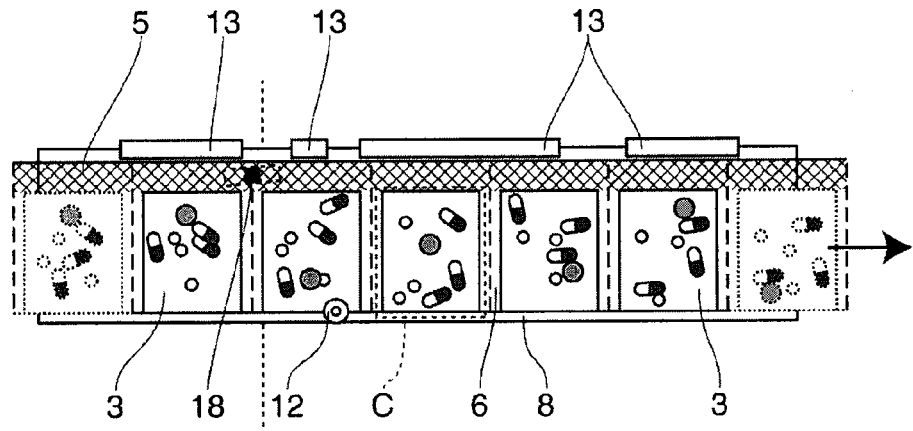
(b)
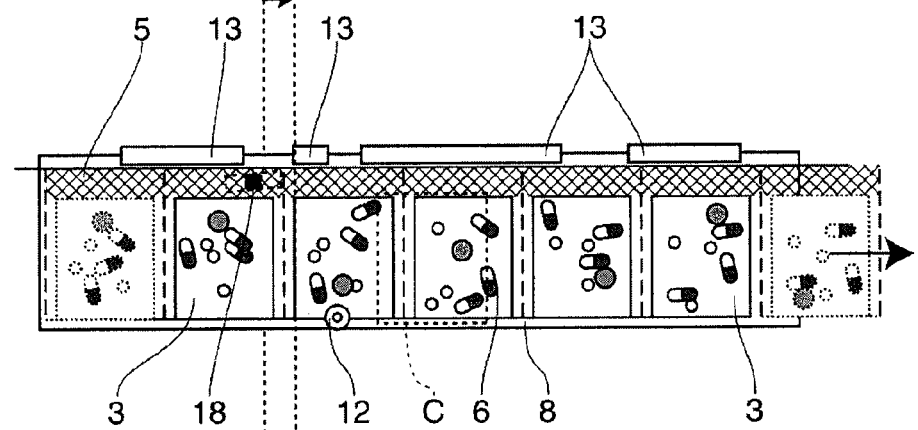
(c)
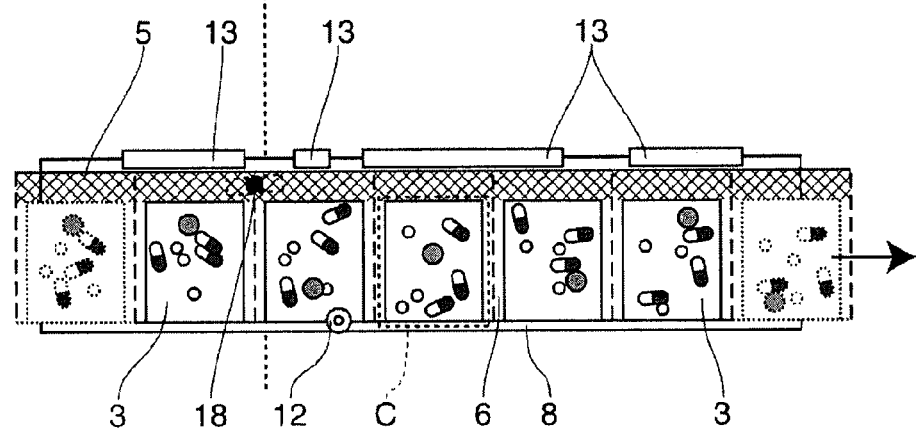

Fig. 7
(a)
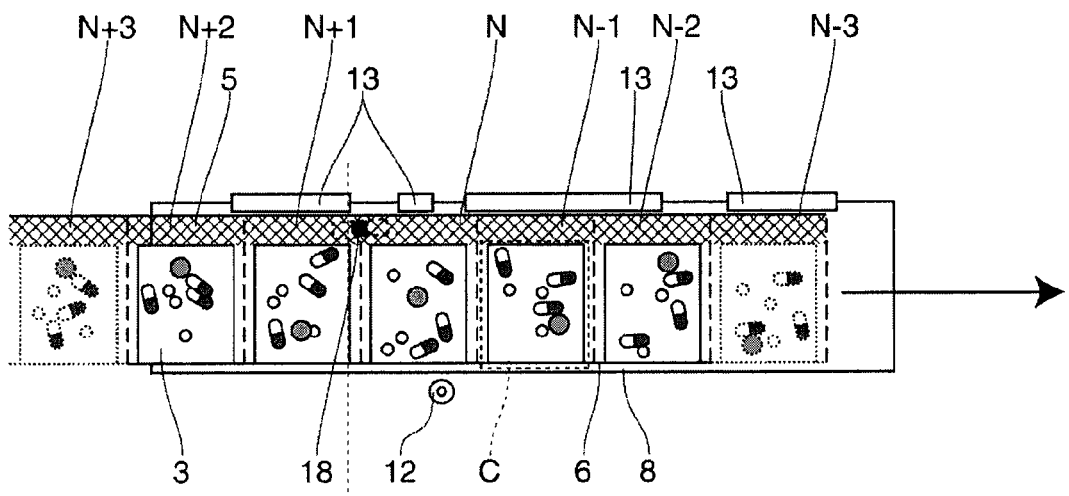
(b)
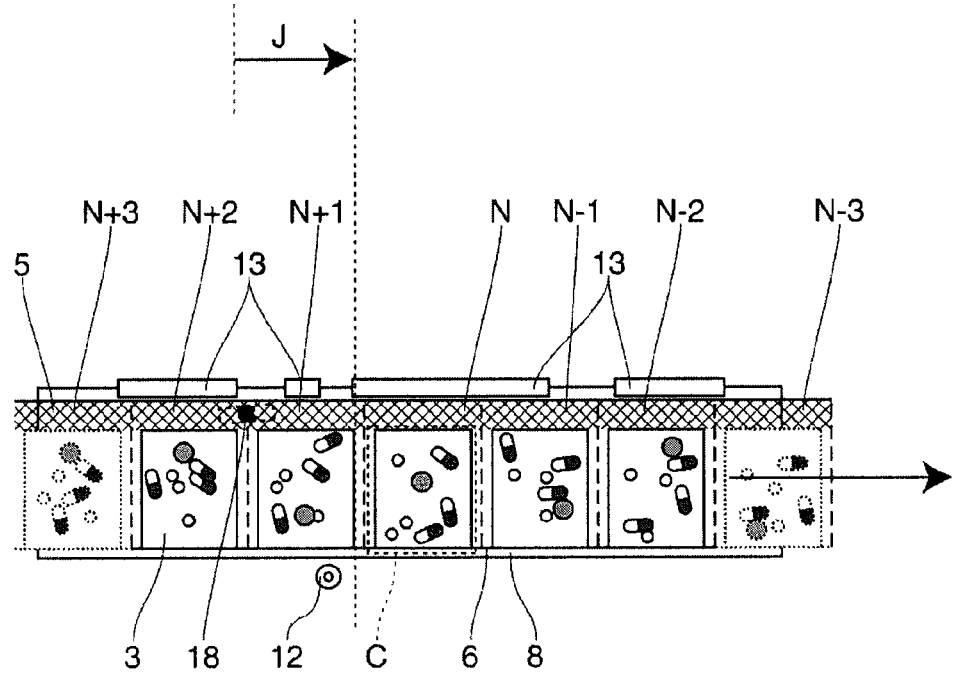

Fig. 9
(a)
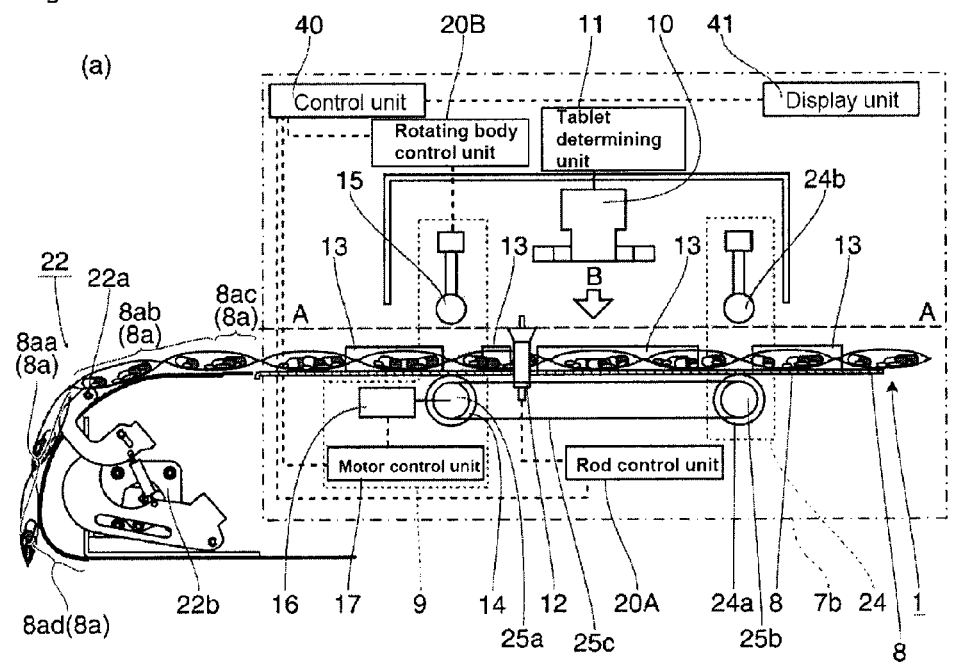
(b)
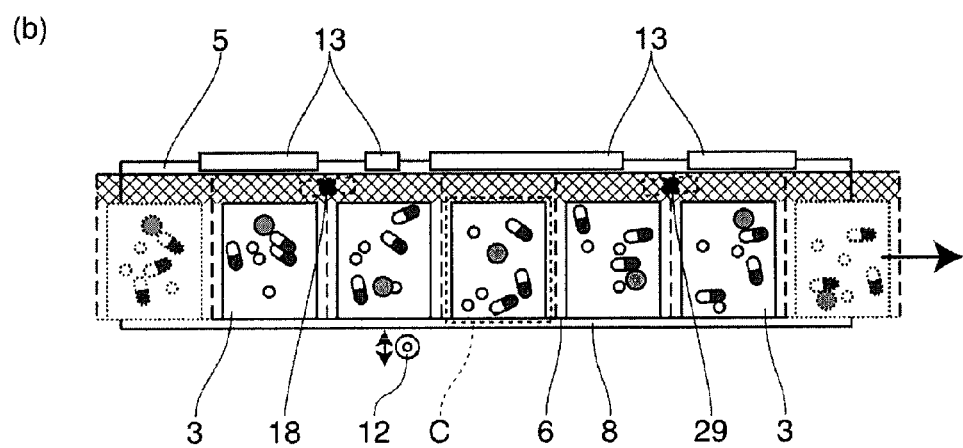

Fig. 16
(a)
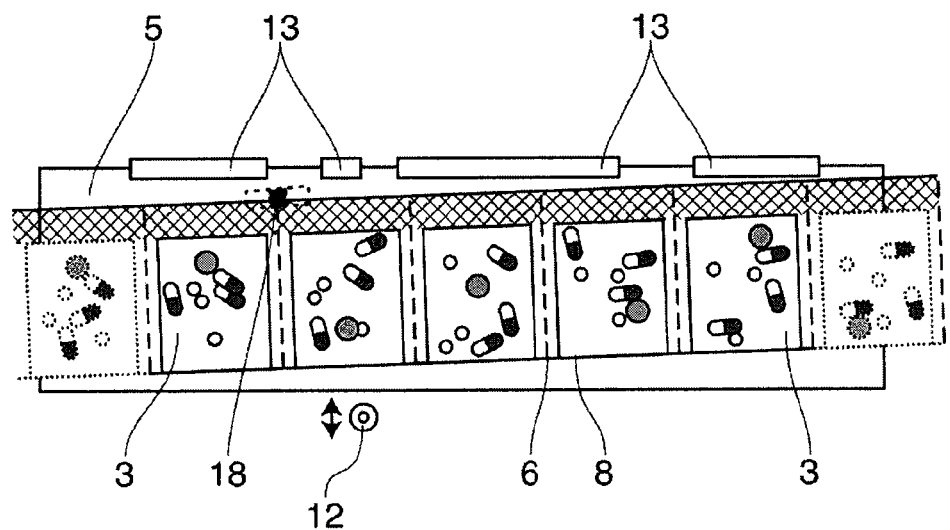
(b)
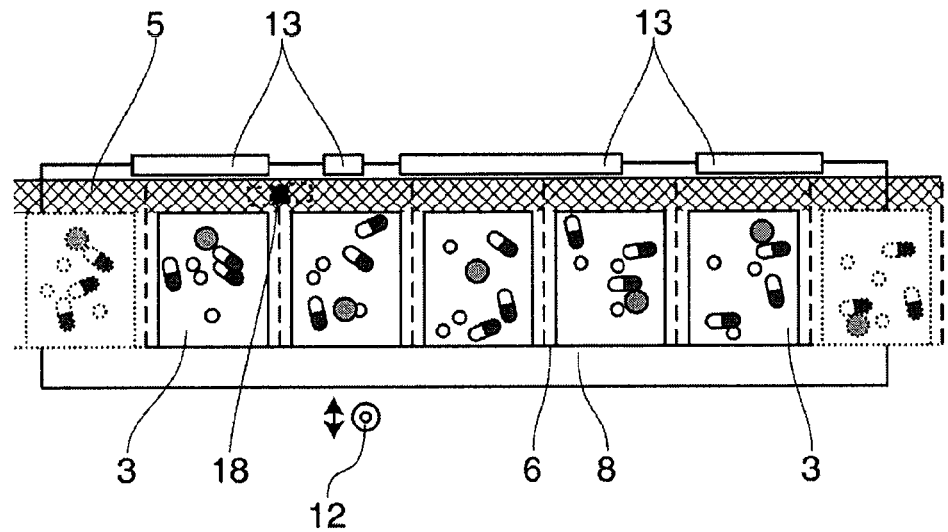

Fig. 18
(a)
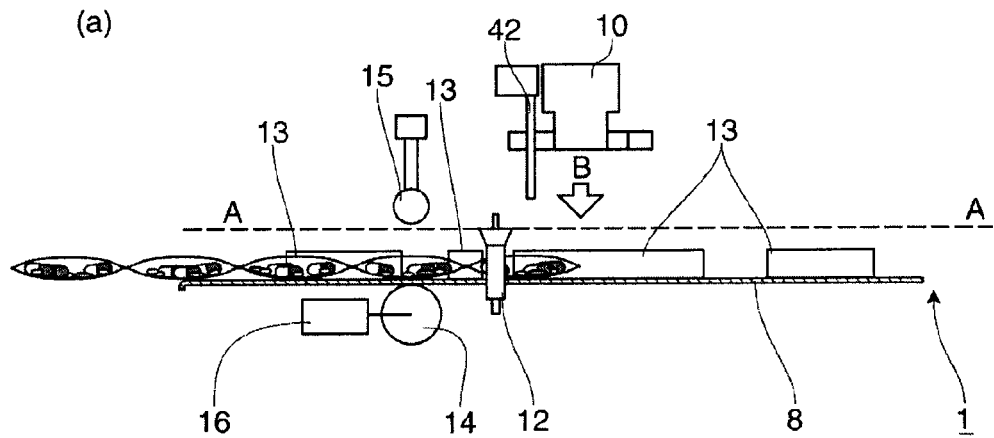
(b)
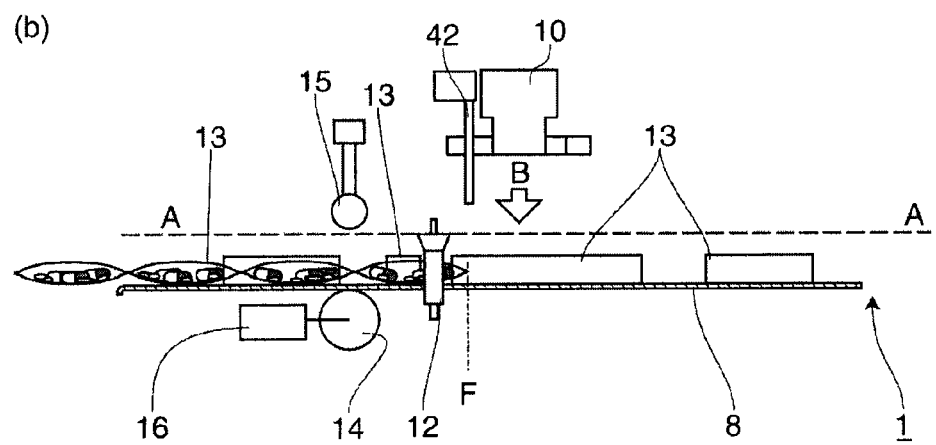
(c)
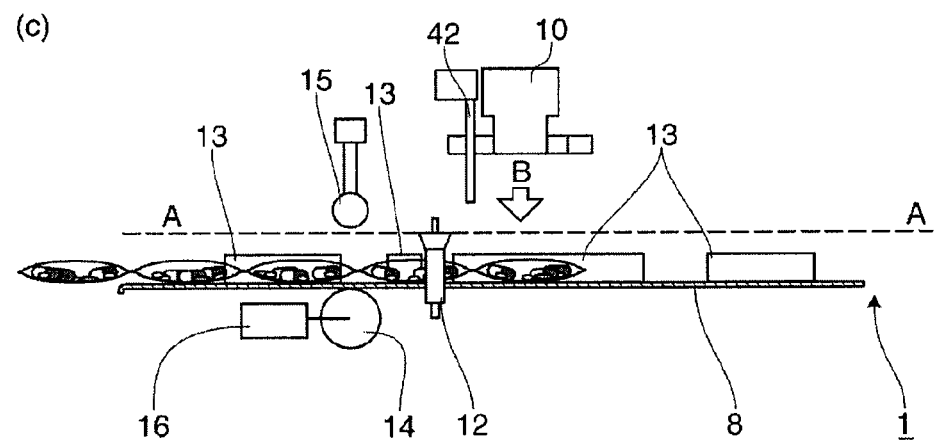

Fig. 19
(a)
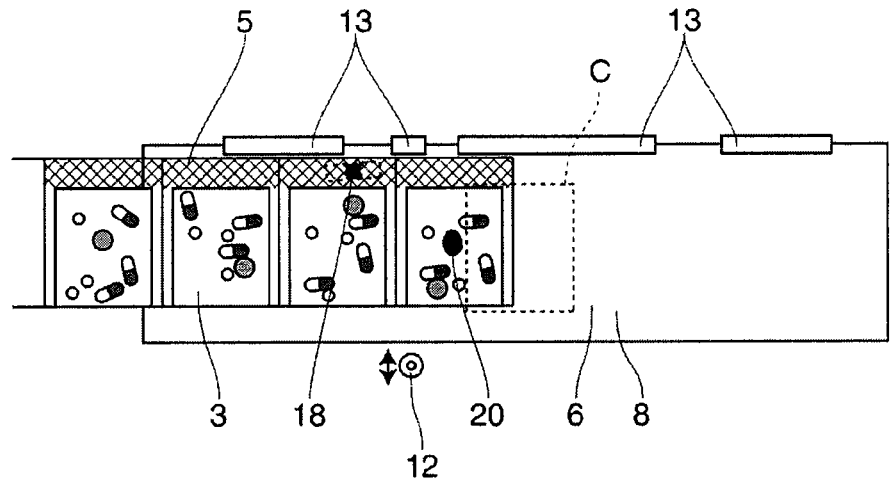
(b)
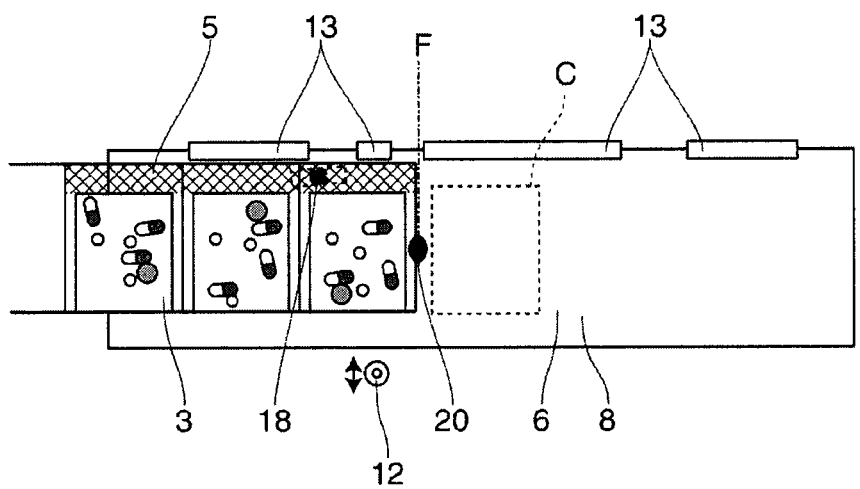
(c)
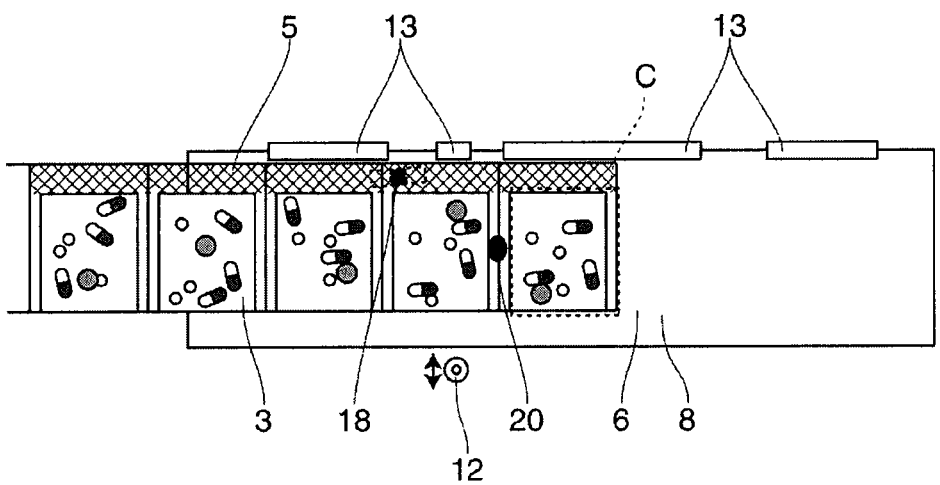

Fig. 23
(a)
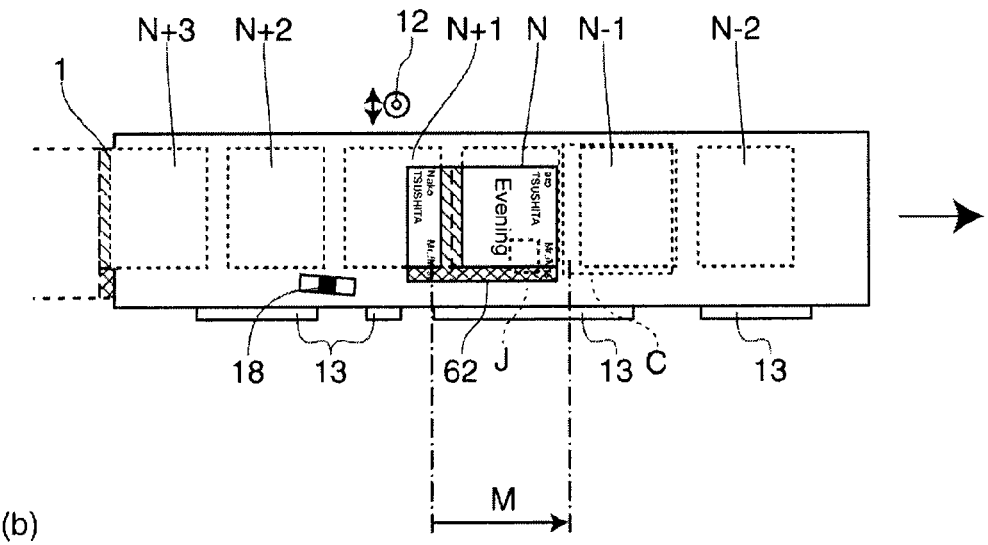
(b)
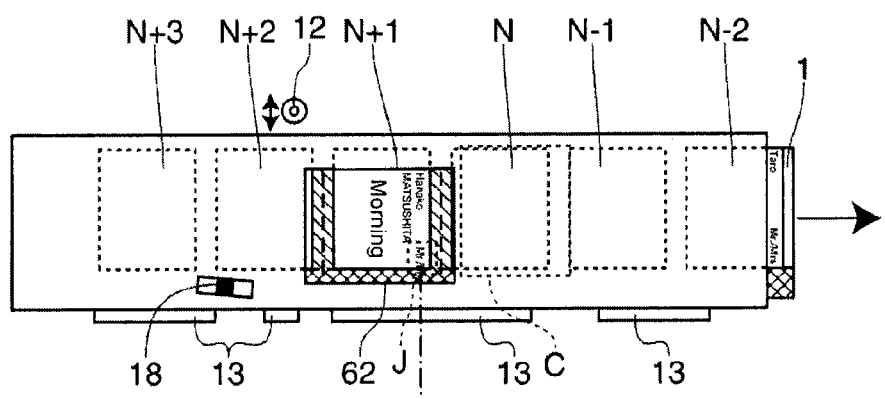
(c)
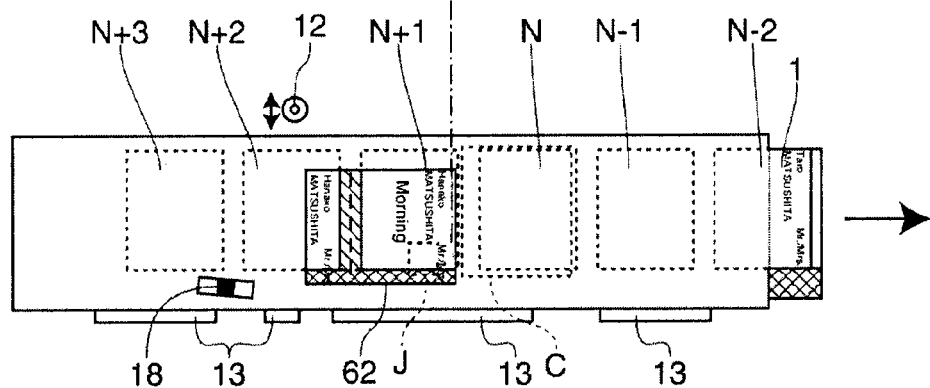

Fig. 24
(a)
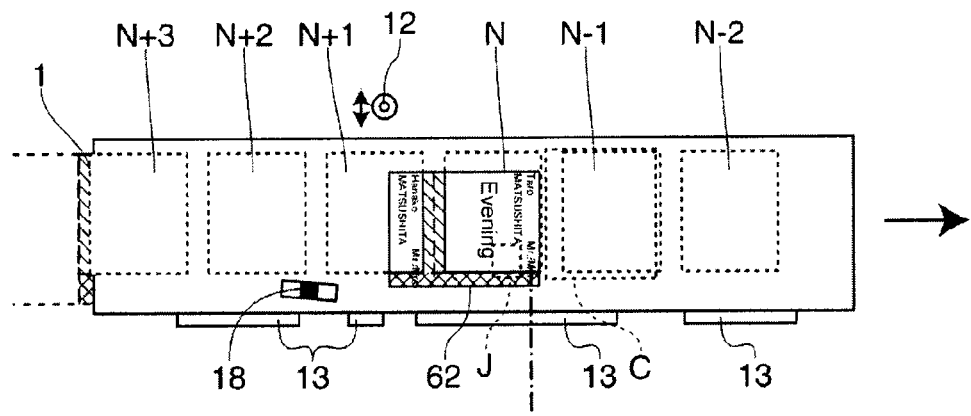
(b)
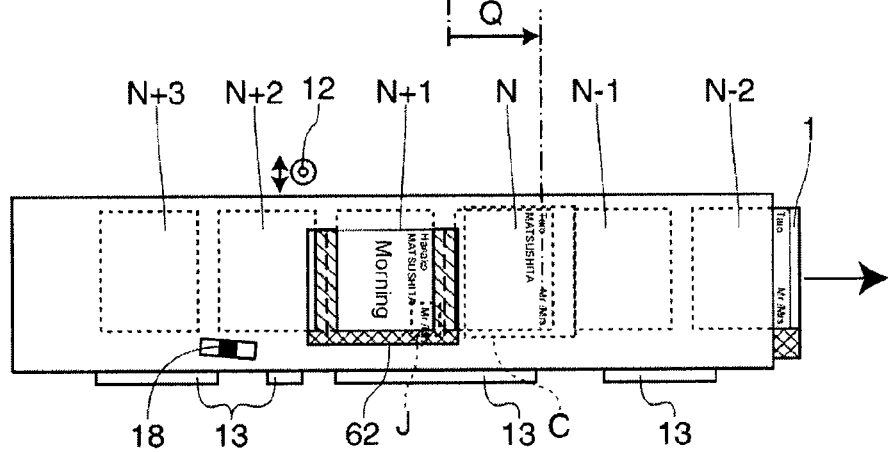

TABLET-INSPECTING DEVICE

TECHNICAL FIELD

The present invention relates to a tablet-inspecting device for inspecting the number of, a kind of and a state of tablets which are included in a drug packet.

BACKGROUND TECHNIQUE

There is known a continuous drug packet in which tablets are included into drug packets based prescription information or the like and the drug packets into which the tablets are included are continuously formed. There is known a tablet counting device for counting the number of drugs included in drug packets of a continuous drug packet.

According to the conventional tablet counting device, in a state where an end of the drug packet is clamped by a clamp mechanism, a looseness-giving mechanism loosens the drug packet clamped by the clamp mechanism, a vibrating mechanism vibrates the drug packet clamped by the clamp mechanism, thereby spreading out tablets in the drug packet clamped by the clamp mechanism and counting the number of drugs (see patent document 1 for example).

Another conventional tablet counting device includes a conveyor path through which a continuous drug packet is conveyed, conveying means for conveying the continuous drug packet along the conveyor path, a determining unit for counting the number of tablets in a drug packet of the continuous drug packet conveyed by the conveying means, and tablet separating means provided upstream of the conveyor path (see patent document 2 for example).

There is known a tablet wrapping device for producing a continuous drug packet in which drug packets each including a tablet separately wrapped in powder wrapping paper sheets are continuously formed based on prescription information or the like (see patent document 3 for example).

Further, as a conventional method for describing information including a result of measurement of the number of tablets on a drug packet or a continuous drug packet (e.g., when tablets of a desired number are not included, this product is marked as a defective), there is a printing method using a printing unit such as a laser printer and an ink-jet printer (see patent document 4 for example).

PRIOR ART DOCUMENTS

Patent Documents

[Patent Document 1] Japanese Patent Application Laid-open No. 2004-236997
[Patent Document 2] Japanese Patent Publication No. 4699563
[Patent Document 3] PCT International Publication No. 2010/041751
[Patent Document 4] PCT International Publication No. 2008/029606

SUMMARY OF THE INVENTION

Problem to be Solved by the Invention

According to patent document 1, periodical vibration (especially periodical vibration of 0.5 to 25 times per second) is given to a drug packet pressed by a clamp mechanism by a vibrating mechanism, and a phenomenon that drugs in the drug packet move to a low region in the drug packet by the periodical vibration occurs.

That is, when periodical vibration is given to the drug packet pressed by the clamp mechanism by the vibrating mechanism, tablets in the drug packet are concentrated on one region in the drug packet (in this case, lowest region in drug packet). Therefore, there is a problem that the number of drugs can not stably be counted.

According to patent document 2, tablets in the drug packet are separated by providing the tablet separating means at an upstream region of the conveyor path, thereby enhancing the counting precision of the number of tablets in the determining unit.

That is, a front surface and a back surface of the drug packet are extremely close to each other and a space therebetween is narrow. Therefore, when a plurality of tablets are included in the drug packet, the tablets are close to each other or superposed on each other.

Hence, in patent document 2, impact is applied to tablets in the drug packet from a back surface of the drug packet, thereby separating the tablets from each other and enhancing the counting precision.

However, since the front surface and the back surface of the drug packet are extremely close to each other and the space therebetween is narrow, even if impact is simply applied to tablets, the tablets are not easily separated from each other and as a result, the counting precision of tablets becomes low.

Further, the continuous drug packet produced by patent document 3 is extremely long (about 7 m as one example), and size variation of drug packets in the continuous drug packet is relatively large (±0.3 cm with respect to 8 cm of one drug packet in longitudinal direction as one example). Therefore, if a drug packet is moved by a predetermined distance (distance of one drug packet), size variations of drug packets are accumulated and this causes an error in a moving distance and as a result, there is a problem that the drug packets can not reliably be moved to an imaging unit which takes an image of a tablet in the drug packet.

Further, according to patent document 4, since black fine particulates (in the case of laser printer) and ink (in the case of ink-jet printer) in which particulates such as carbon and plastic are mixed are used as printing material, a drug packet or a continuous drug packet is made dirty in some cases when information is printed.

Hence, it is an object of the present invention to provide a tablet-inspecting device capable of enhancing determining precision of the number of tablets or kinds of tablet, and capable of stably inspecting drugs.

It is another object of the invention to provide a tablet-inspecting device capable of reliably moving drug packets in a continuous drug packet to a position where an image is taken.

It is another object of the invention to prevent a drug packet and a continuous drug packet from being made dirty when information is recorded on the drug packet and the continuous drug packet.

Means for Solving the Problem

A first aspect of the invention provides a tablet-inspecting device comprising a conveyor path on which a continuous drug packet composed of a plurality of drug packets arranged in a row moves, a continuous drug packet-driving unit for moving the continuous drug packet from an upstream side to a downstream side of the conveyor path, an imaging unit for taking an image of tablets included in the drug packet, and a tablet determining unit for inspecting the tablets based on the image of the tablets taken by the imaging unit, wherein the continuous drug packet-driving unit is disposed more upstream of the conveyor path than the imaging unit, a rod unit which is pressed against a side portion of the drug packet is disposed between the continuous drug packet-driving unit and the imaging unit, the tablet-inspecting device further comprises a rod control unit for operating the rod unit, and a control unit for giving operation instructions to the continuous drug packet-driving unit and the rod control unit, the control unit gives, to the continuous drug packet-driving unit, operation instructions to move the continuous drug packet from the upstream side to the downstream side of the conveyor path, and reciprocating operation instructions to alternately move the continuous drug packet to the upstream side and the downstream side of the conveyor path, the control unit gives, to the rod control unit, rod unit-pressing operation instructions to press the rod unit against the side portion of the drug packet, and when the control unit gives the reciprocating operation instructions to the continuous drug packet-driving unit, the control unit has given the rod unit -pressing operation instructions to the rod control unit.

According to a second aspect of the invention, in the tablet-inspecting device of the first aspect, an introduction path is provided upstream of the conveyor path, tablet separating means is disposed on the introduction path, the tablet separating means includes a rod crossing the introduction path, and a driving unit for alternately moving the rod to an upstream side and a downstream side of the introduction path, a portion of the introduction path located more upstream than a moving range of the rod is set lower than a portion of the introduction path located in the moving range of the rod, and the rod abuts against a lower surface of the continuous drug packet.

According to a third aspect of the invention, in the tablet-inspecting device of the first aspect, tablet separating means is disposed more upstream than an upstream end of the conveyor path, the tablet separating means includes vibrating means disposed above the conveyor path, and a vibration space provided between the vibrating means and the upstream end of the conveyor path, and a length of the vibration space from the vibrating means to the conveyor path is set longer than a length of the drug packet in a conveying direction.

According to a fourth aspect of the invention, in the tablet-inspecting device of any one of the first to third aspects, a clamped portion formed by superposing powder wrapping paper sheets on each other and clamping the powder wrapping paper sheets is formed on one of sides of the continuous drug packet in its longitudinal direction, a folded back portion formed by folding back the powder wrapping paper sheets is formed on an other side of the continuous drug packet in the longitudinal direction, the continuous drug packet is composed of a first rotating body disposed on a lower portion of the conveyor path, a second rotating body disposed on an upper portion of the conveyor path, and a motor unit connected to the first rotating body, and the first rotating body and the second rotating body are in contact with the clamped portion.

According to a fifth aspect of the invention, in the tablet-inspecting device of the fourth aspect, a guide is provided on at least one side surface of the conveyor path, and a rotation shaft of at least one of the first rotating body and the second rotating body is oriented to such a direction that discharging directions of the first rotating body and the second rotating body approach the guide.

According to a sixth aspect of the invention, in the tablet-inspecting device of any one of the first to fifth aspects, the rod unit includes a columnar first rotating unit, and the first rotating unit comes into contact with a side surface of the drug packet, thereby rotating the first rotating unit in tandem with a reciprocating operation of the continuous drug packet.

According to a seventh aspect of the invention, in the tablet-inspecting device of the sixth aspect, the rod unit includes a truncated conical second rotating unit at a location higher than the first rotating unit, and the second rotating unit rotates in tandem with the reciprocating operation of the continuous drug packet.

According to an eighth aspect of the invention, in the tablet-inspecting device of the third aspect, a guide path extending from an upstream side of the tablet separating means toward the tablet separating means is upwardly tilted.

According to a ninth aspect of the invention, in the tablet-inspecting device of the eighth aspect, the upstream end of the conveyor path is downwardly tilted.

According to a tenth aspect of the invention, in the tablet-inspecting device of any one of the third, eighth and ninth aspects, the vibrating means includes a roller which rotates in a travelling direction of the continuous drug packet, and a vibrating motor for vibrating the roller, wherein the continuous drug packet is placed on an outer surface of the roller.

According to an eleventh aspect of the invention, in the tablet-inspecting device of the tenth aspect, the continuous drug packet is supplied toward the roller from a location on an upstream side of the roller and lower than the roller.

According to a twelfth aspect of the invention, in the tablet-inspecting device of the fourth aspect, the first rotating body is made of rubber, and the second rotating body is made of plastic.

According to a thirteenth of the invention, in the tablet-inspecting device of any one of the first to twelfth aspects, a continuous drug packet detecting unit for detecting the continuous drug packet is disposed more upstream of the conveyor path than the imaging unit, the control unit gives, to the continuous drug packet-driving unit, forward operation instructions to move the continuous drug packet from the upstream side to the downstream side of the conveyor path, and backward operation instructions to move the continuous drug packe from the downstream side to the upstream side of the conveyor path, if the continuous drug packet detecting unit detects the continuous drug packet after the continuous drug packet is thrown, the control unit gives the backward operation instructions, while the continuous drug packet detecting unit is detecting the continuous drug packet after the backward operation instructions, the control unit keeps giving the backward operation instructions, when the continuous drug packet detecting unit does not detect the continuous drug packet, the control unit stops giving the backward operation instructions, thereby disposing the continuous drug packet at a first initial position, after the continuous drug packet is disposed at the first initial position, the control unit gives the forward operation instructions thereby moving the continuous drug packet to a second initial position, and after the continuous drug packet is disposed at the second initial position, the control unit makes the imaging unit take an image.

According to a fourteenth aspect of the invention, in the tablet-inspecting device of any one of the first to twelfth aspects, a drug packet detecting unit for detecting a symbol or a character printed on each of the drug packets is disposed on the conveyor path.

According to a fifteenth aspect of the invention, in the tablet-inspecting device of the fourteenth aspect, the control unit carries out a first conveying operation for moving the continuous drug packet by a first moving distance after the imaging unit takes an image, and if the drug packet detecting unit detects the symbol or the character during the first conveying operation, the control unit carries out a second conveying operation for moving the continuous drug packet by a second moving distance after the detection.

According to a sixteenth aspect of the invention, in the tablet-inspecting device of the fifteenth aspect, the second moving distance is set smaller than the first moving distance.

According to a seventeenth aspect of the invention, in the tablet-inspecting device of the fifteenth or sixteenth aspect, if the tablet-inspecting device is in a non-detected state where the drug packet detecting unit can not detect the symbol or the character during the first conveying operation, the control unit carried out a third conveying operation for moving the continuous drug packet by a third moving distance when predetermined time is elapsed after the first conveying operation is started.

According to an eighteenth aspect of the invention, in the tablet-inspecting device of the seventeenth aspect, when the third conveying operation is carried out for predetermined continuous some of the drug packets, the control unit stops the continuous drug packet-driving unit.

According to a nineteenth aspect of the invention, in the tablet-inspecting device of the first aspect, the tablet-inspecting device further includes recess forming means for forming a recess in the continuous drug packet, and the control unit makes the recess forming means form the recess in the continuous drug packet based on a result of a inspecting operation carried out by the tablet determining unit.

According to a twentieth aspect of the invention, in the tablet-inspecting device of the nineteenth aspect, a clamped portion formed by superposing powder wrapping paper sheets on each other and clamping the powder wrapping paper sheets is formed on one of sides of the continuous drug packet in its longitudinal direction, a folded back portion formed by folding back the powder wrapping paper sheets is formed on an other side of the continuous drug packet in the longitudinal direction, and the recess is formed in the clamped portion.

A twenty-first aspect of the invention provides a drug packet inspected using the tablet-inspecting device according to the nineteenth or twentieth aspect, the recess is formed in the drug packet.

A twenty-second aspect of the invention provides a continuous drug packet inspected using the tablet-inspecting device according to the nineteenth or twentieth aspect, the recess is formed in any of the drug packets.

A twenty-third aspect of the invention provides a tablet-inspecting device comprising a conveyor path on which a continuous drug packet composed of a plurality of drug packets arranged in a row moves, a continuous drug packet-driving unit for moving the continuous drug packet from an upstream side to a downstream side of the conveyor path, an imaging unit for taking an image of tablets included in the drug packet, and a tablet determining unit for inspecting the tablets based on the image of the tablets taken by the imaging unit, wherein an introduction path is provided upstream of the conveyor path, tablet separating means is disposed on the introduction path, the tablet separating means includes a rod crossing the introduction path, and a driving unit for alternately moving the rod to an upstream side and a downstream side of the introduction path, a portion of the introduction path located more upstream than a moving range of the rod is set lower than a portion of the introduction path located in the moving range of the rod, and the rod abuts against a lower surface of the continuous drug packet.

Effect of the Invention

According to the present invention, it is possible to stably count the number of drugs.

That is, in the invention, the rod unit presses the side surface of the drug packet to widen the space in the drug packet. In this state, the continuous drug packet is made to straightly reciprocate with respect to the moving direction of the continuous drug packet, thereby making it possible to disperse, within the drug packet, tablets in the drug packet. Therefore, it is possible to prevent tablets in the drug packet from concentrating on one region within the drug packet. As a result, it is possible to provide a tablet-inspecting device capable of stably counting the number of drugs.

Further, the invention includes the vibrating means disposed above the conveyor path on an upstream side of the conveyor path, and the vibration space provided between the vibrating means and the conveyor path, and a length from the vibrating means of the vibration space to the conveyor path is set longer than a length of the drug packet in the conveying direction. Therefore, the drug packet is vibrated by the vibrating means, and the vibrating means is vertically largely vibrated in a next vibration space. As a result, a plurality of tablets included in this drug packet are appropriately separated from each other and according to this, it is possible to enhance the determining precision of the number of tablets or the kinds of tablet of the determining unit on the downstream side.

In the invention, the first rotating body is made of rubber and the second rotating body is made of plastic. Therefore, even if a throwing direction (conveying direction) of the continuous drug packet is deviated, although the continuous drug packet once comes into contact with the guide, since a friction coefficient between the second rotating body and the continuous drug packet is small, the continuous drug packet once temporarily "slips", and the throwing direction (conveying direction) of the continuous drug packet is naturally corrected to a desired direction by the "slip". Therefore, in the configuration of the invention, precision of the throwing direction (conveying direction) of the continuous drug packet is not required.

Hence, it is possible to simplify the configuration of the conveying means in the tablet-inspecting device and as a result, it is possible to reduce a production cost of the tablet-inspecting device.

According to the invention, it is possible to easily set up the continuous drug packet to an initial position where the counting operation of the number of tablets in the drug packet in the tablet-inspecting device is started.

That is, in the invention, after the continuous drug packet is manually thrown (by human's hand) by the continuous drug packet detecting unit, if the continuous drug packet detecting unit detects a continuous drug packet, backward operation is carried out, and when the continuous drug packet detecting unit does not detect a continuous drug packet any more, the backward operation instructions are stopped and the continuous drug packet is disposed at the first initial position. After the continuous drug packet is disposed at the first initial position, forward operation is carried out and the continuous drug packet is moved to a second initial position, and after the continuous drug packet is disposed at the second initial position, the imaging unit takes an image of the drug packet. As a result, it is possible to easily start the counting operation for counting the number of tablets in a drug packet in the tablet-inspecting device, and to set up the continuous drug packet to the initial position where the counting operation of the number of tablets in the drug packet in the tablet-inspecting device is started.

According to the invention, it is possible to precisely move each of drug packets in a continuous drug packet to a region where the imaging unit takes an image of the drug packet.

That is, in the invention, a symbol or a character described in each of drug packets in a continuous drug packet is detected and based on the detected information, each of the drug packets can be moved (conveyed) to a region where the imaging unit takes an image of the drug packet in the continuous drug packet.

Even if a detection error of a drug packet detecting unit is caused due to a stain or a wrinkle on a drug packet, it is possible to move each of the drug packets to a region where the number of tablets can be counted by controlling time. As a result, it is possible to reduce variation in conveying distance (moving distance) of a continuous drug packet per one counting operation of the number of tablets caused by size variation of the drug packets in the continuous drug packet, and it is possible to reliably move the drug packet in the continuous drug packet to the region where the imaging unit takes an image of each of the drug packets in the continuous drug packet.

According to the invention, it is possible to prevent a drug packet and a continuous drug packet from being made dirty when information is recorded on the drug packet or the continuous drug packet, and it is possible to reduce a production cost.

That is, in the invention, a recess is formed in a drug packet or a continuous drug packet. According to this, it is possible to determine whether tablets of a desired number are included in the drug packet or the continuous drug packet (it is possible to determine whether the product is a good product or a defective). Hence, after black fine particulates in which particulates such as carbon and plastic are mixed and printing material such as ink are eliminated, a mark can be formed on a drug packet or a continuous drug packet in which tablets of a desired number are not included. As a result, it is possible to prevent a drug packet and a continuous drug packet from being made dirty.

BRIEF DESCRIPTION OF THE DRAWINGS

FIG. 3 are plan view for explaining a rod unit-pressing operation of the tablet-inspecting device;

FIG. 4 are sectional views in a position of the rod unit shown in FIG. 3;

FIG. 5 are plan views for explaining reciprocating operation of the tablet-inspecting device;

FIG. 7 are plan views showing a drug packet-sending operation of the tablet-inspecting device;

FIG. 9(a) is a partial sectional side view showing an outline configuration of a tablet-inspecting device in a second embodiment of the invention, and FIG. 9(b) is a plan view of a surface A-A in FIG. 9(a) as viewed from an arrow B (from above);

FIG. 16 are plan views showing a state of a drug continuous body in the tablet-inspecting device;

FIG. 18 are sectional views showing a state where a continuous drug packet in the tablet-inspecting device is thrown by a manual operation;

FIG. 19 are plan views of a surface A-A in FIG. 18 as viewed from B;

FIG. 23 are bottom views showing motion of a continuous drug packet when a symbol could be detected by the tablet-inspecting device of the embodiment;

FIG. 24 are bottom views showing motion of the continuous drug packet when a symbol could not be detected by the tablet-inspecting device of the embodiment.

Figure 1:
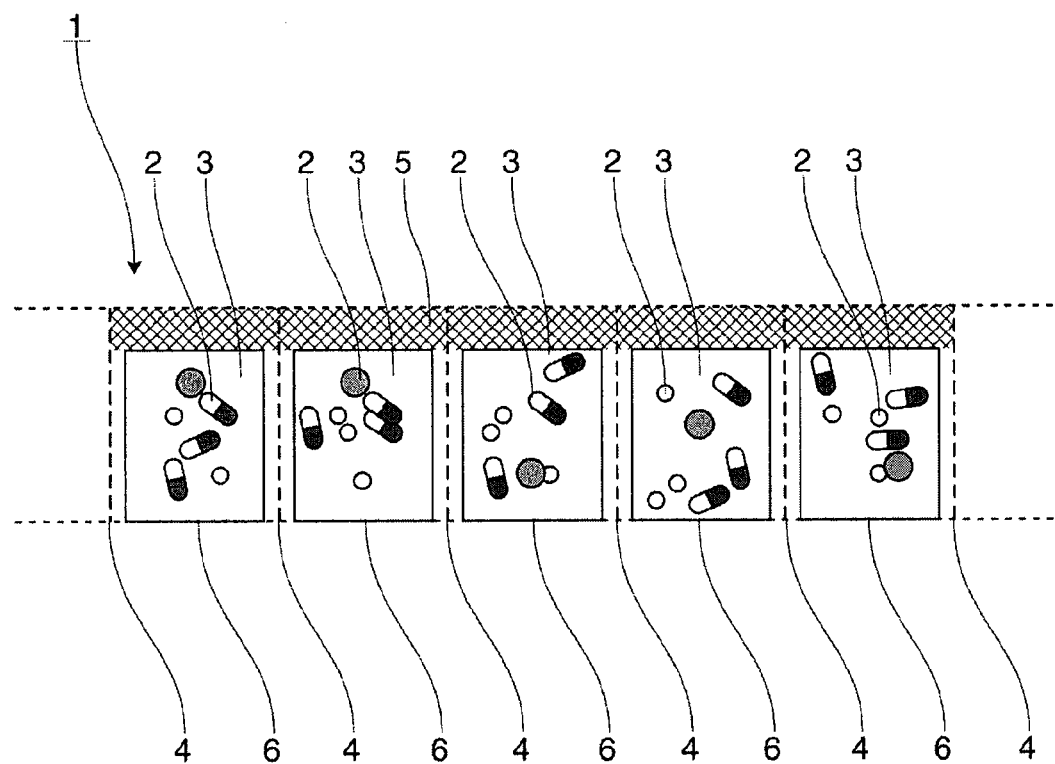
FIG. 1 is a plan view of a continuous drug packet used in a tablet-inspecting device according to embodiments of the present invention.

EXPLANATION OF SYMBOLS 1 continuous drug packet
2 tablet
3 drug packet
7a tablet-inspecting device
8 conveyor path
9 continuous drug packet-driving unit
10 imaging unit
11 tablet determining unit
12 rod unit
13 guide
14 first rotating body
15 second rotating body
16 motor unit 17 motor control unit
20A rod control unit
20B rotor control unit
40 control unit Mode For Carrying Out The Invention An embodiment of the present invention will be described below together with the drawings.

First, a continuous drug packet used in the embodiment will be described.

FIG. 1 is a plan view of the continuous drug packet.

The continuous drug packet 1 is composed of a plurality of drug packets 3 arranged in a row. One or more tablets 2 are included in each of the drug packets 3. A perforation 4 is formed between the drug packets 3.

Powder wrapping paper sheets for forming the drug packets 3 are superposed and clamped on one another, thereby forming a clamped portion 5 on one side of the continuous drug packet 1 in its longitudinal direction.

Folded back portions 6 are formed on an other side of the continuous drug packet 1 in the longitudinal direction by folding back the powder wrapping paper sheets forming the drug packets 3.

At least one of surfaces (upper surface) of the drug packet 3 is transparent or translucent, and it is possible to visually inspect the tablets 2 included in the drug packet 3. For example, see-through white color can be used as the translucent.

(First Embodiment)

A tablet-inspecting device in a first embodiment of the present invention will be described using FIGS. 2 to 7.

FIG. 2(a) is a partial sectional side view showing an outline configuration of the tablet-inspecting device in the first embodiment, FIG. 2(b) is a plan view of a surface A-A in FIG. 2(a) as viewed from an arrow B (from above), and FIG. 2(c) is an enlarged view of essential portions in FIG. 2(b).

The tablet-inspecting device 7a includes a conveyor path 8 through which the continuous drug packet 1 moves, a continuous drug packet-driving unit 9 for moving the continuous drug packet 1, an imaging unit 10 for taking images of the plurality of tablets 2 included in the drug packet 3, and a tablet determining unit 11 for inspecting the shoot tablets 2.

The continuous drug packet 1 is thrown from upstream of the conveyor path 8 and moves from an upstream side (left side in FIG. 2) to a downstream side (right side in FIG. 2) of the conveyor path 8.

The continuous drug packet-driving unit 9 is disposed more upstream of the conveyor path 8 than the imaging unit 10.

The tablet determining unit 11 inspects the number of tablets, kinds of tablet and a state of tablets based on the images of the tablets 2 taken by the imaging unit 10.

The tablet-inspecting device 7a includes a rod unit 12 for carrying out a pressing operation with respect to a side of the drug packet 3, guides 13 for restraining the continuous drug packet 1 from moving, a rod control unit 20A for operating the rod unit 12, a rotating body control unit 20B for vertically moving the second rotating body 15, and a control unit 40. The control unit 40 gives operation instructions to the continuous drug packet-driving unit 9, the rod control unit 20A and the rotating body control unit 20B.

The rod unit 12 is disposed between the continuous drug packet-driving unit 9 and the imaging unit 10. That is, the rod unit 12 is disposed more downstream of the conveyor path 8 than the continuous drug packet-driving unit 9 and more upstream of the conveyor path 8 than the imaging unit 10.

The rod unit 12 is disposed at a position where the rod unit 12 does not come into contact with the continuous drug packet 1, and the rod unit 12 is moved, by the rod control unit 20A, to a position where the side of the continuous drug packet 1 is pressed. For moving the rod unit 12, it is possible to employ a configuration that the rod unit 12 is made to approach or separate from the continuous drug packet 1 by tilting the rod unit 12, or a configuration that the rod unit 12 is made to approach or separate from the continuous drug packet 1 moving the rod unit 12 in parallel.

The guides 13 are provided on at least one of side surfaces of the conveyor path 8.

As shown in this embodiment, when the guides 13 are provided on one of the side surfaces of the conveyor path 8, the rod unit 12 is disposed on the other side surface of the conveyor path 8, and the continuous drug packet 1 is thrown into the conveyor path 8 such that the clamped portion 5 is located on the side of the guides 13.

When the guides 13 are provided on both side surfaces of the conveyor path 8, the continuous drug packet 1 is thrown into the conveyor path 8 such that the folded back portion 6 is located on the side of the rod unit 12.

The continuous drug packet-driving unit 9 includes a first rotating body 14 disposed on a lower portion of the conveyor path 8, the second rotating body 15 disposed on an upper portion of the conveyor path 8, a motor unit 16 connected to the first rotating body 14, and a motor control unit 17 for controlling the motor unit 16.

The first rotating body 14 and the second rotating body 15 are disposed at positions of the clamped portion 5.

The first rotating body 14 rotates such that the first rotating body 14 pushes up the clamped portion 5 of the continuous drug packet 1 from its lower surface. The second rotating body 15 is lowered by the rotating body control unit 20B, thereby pressing the clamped portion 5 of the continuous drug packet 1 from its upper surface. The second rotating body 15 is pressed against the continuous drug packet 1, and rotated by the first rotating body 14.

The control unit 40 gives operation instructions to the motor control unit 17 to move the continuous drug packet 1 from the upstream side to the downstream side of the conveyor path 8, and gives reciprocating operation instructions for alternately moving the continuous drug packet 1 to the upstream side and the downstream side of the conveyor path 8.

When the control unit 40 gives instructions to the rod control unit 20A to press the rod unit 12 against a side portion of the drug packet 3, the control unit 40 gives instructions to the rotating body control unit 20B to lower the second rotating body 15, and gives reciprocating operation instructions to the motor control unit 17.

By the instructions from the control unit 40, the continuous drug packet-driving unit 9 carries out a drug packet-sending operation of the continuous drug packet 1 and reciprocating operation in the moving direction of the continuous drug packet 1. The drug packet-sending operation of the continuous drug packet 1 and the reciprocating operation in the moving direction of the continuous drug packet 1 will be described later.

To press the rod unit 12 against the side portion of the drug packet 3, and to make the motor control unit 17 to carry out the reciprocating operation function as first tablet separating means in this embodiment.

In this embodiment, as shown in FIG. 2(b), a first contact portion 18 on the clamped portion 5 of the continuous drug packet 1 is sandwiched between the first rotating body 14 and the second rotating body 15. Tablets 2 do not exist on the clamped portion 5 of the continuous drug packet 1. Therefore, by sandwiching the first contact portion 18 on the clamped portion 5 between the first rotating body 14 and the second rotating body 15, it is possible to prevent tablets 2 from being damaged.

As shown in FIG. 2(b), a region where the imaging unit 10 takes images is a region surrounded by dotted lines C. A space in the drug packet 3 in which tablets 2 are included corresponds to the region surrounded by the dotted lines C, but the region where the imaging unit 10 takes images may be wider than the space in the drug packet 3.

The tablet-inspecting device 7a in this embodiment includes second tablet separating means 22 in addition to the first tablet separating means.

An introduction path 8a is provided upstream of the conveyor path 8. The second tablet separating means 22 is disposed in the introduction path 8a.

The second tablet separating means 22 includes a rod 22a crossing the introduction path 8a, and a driving unit 22b which alternately moves the rod 22a to the upstream side and the downstream side of the introduction path 8a.

The introduction path 8a is composed of an introduction path 8aa located upstream of a moving range of the rod 22a, an introduction path 8ab in the moving range of the rod 22a, and an introduction path 8ac located downstream of the moving range of the rod 22a.

A downstream end of the introduction path 8ac is connected to an upstream end of the conveyor path 8.

The introduction path 8ac, the introduction path 8ab and the introduction path 8aa are made of plate materials such as stainless steel, and they are continuous from one another through curved surfaces.

The introduction path 8a is formed such that a downstream end of the introduction path 8ac is located at the highest position, and an upstream end of the introduction path 8aa is located at the lowest position.

The upstream end of the introduction path 8aa includes a curved surface portion 8ad exceeding a vertical surface.

The rod 22a abuts against a lower surface of the continuous drug packet 1.

As described above, the introduction path 8aa located more upstream than the moving range of the rod 22a is formed lower than the introduction path 8ab located in the moving range of the rod 22a.

Therefore, in a state where one end of the continuous drug packet 1 is thrown into the conveyor path 8, the continuous drug packet 1 located more upstream than the rod 22a hangs down by its own weight, and tension is applied to the continuous drug packet 1 located in the moving range of the rod 22a.

The second tablet separating means 22 can disperse the tablets 2 by reciprocating the rod 22a on the lower surface of the continuous drug packet 1 to which the tension is applied.

Since the tablet-inspecting device 7a of the embodiment includes the curved surface portion 8ad, the continuous drug packet 1 which hangs down by its own weight can be prevented from being damaged.

As shown in FIG. 2(c), the first rotating body 14 is provided with a rotation shaft such that a discharging direction discharged by the first rotating body 14 becomes a direction approaching the guide 13.

By tilting the rotation shaft of the first rotating body 14 like this, the continuous drug packet 1 is sent out from the first rotating body 14 such that the continuous drug packet 1 approaches the guide 13. If the continuous drug packet 1 which is discharged such that it approaches the guides 13 abuts against the guide 13, the continuous drug packet 1 moves along the guide 13 thereafter.

Therefore, in this embodiment, the continuous drug packet 1 moves along the guide 13, the continuous drug packet 1 does not separate from the guide 13, and it is possible to reliably position the continuous drug packet 1 in the conveyor path 8.

Like the rotation shaft of the first rotating body 14, a rotation shaft of the second rotating body 15 may also be provided such that a discharging direction discharged by the second rotating body 15 becomes a direction approaching the guide 13. Alternatively, the rotation shaft of only the second rotating body 15 may be provided such that the discharging direction discharged by the second rotating body 15 becomes the direction approaching the guide 13 instead of the first rotating body 14.

In this embodiment, the control unit 40 gives operation instructions to the imaging unit 10, the tablet determining unit 11 and the second tablet separating means 22, and the control unit 40 makes a display unit 41 display contents of the operation instructions and a result of the operation. The control unit 40 controls ON/OFF operation of the driving unit 22b of the second tablet separating means 22.

Next, an operation of the tablet-inspecting device in the embodiment will be described using FIGS. 3 to 7.

A rod-pressing operation will be described below.

FIG. 3(a) is a plan view of the tablet-inspecting device before the rod-pressing operation, and FIG. 3(b) is a plan view of the tablet-inspecting device after the rod-pressing operation.

FIG. 4 are sectional views in a position of the rod in FIG. 3, wherein FIG. 4(a) is a sectional view of the tablet-inspecting device before the rod-pressing operation, FIG. 4(b) is a sectional view of the tablet-inspecting device during the rod-pressing operation and FIG. 4(c) is a sectional view of the tablet-inspecting device after the rod-pressing operation.

Figure 2:
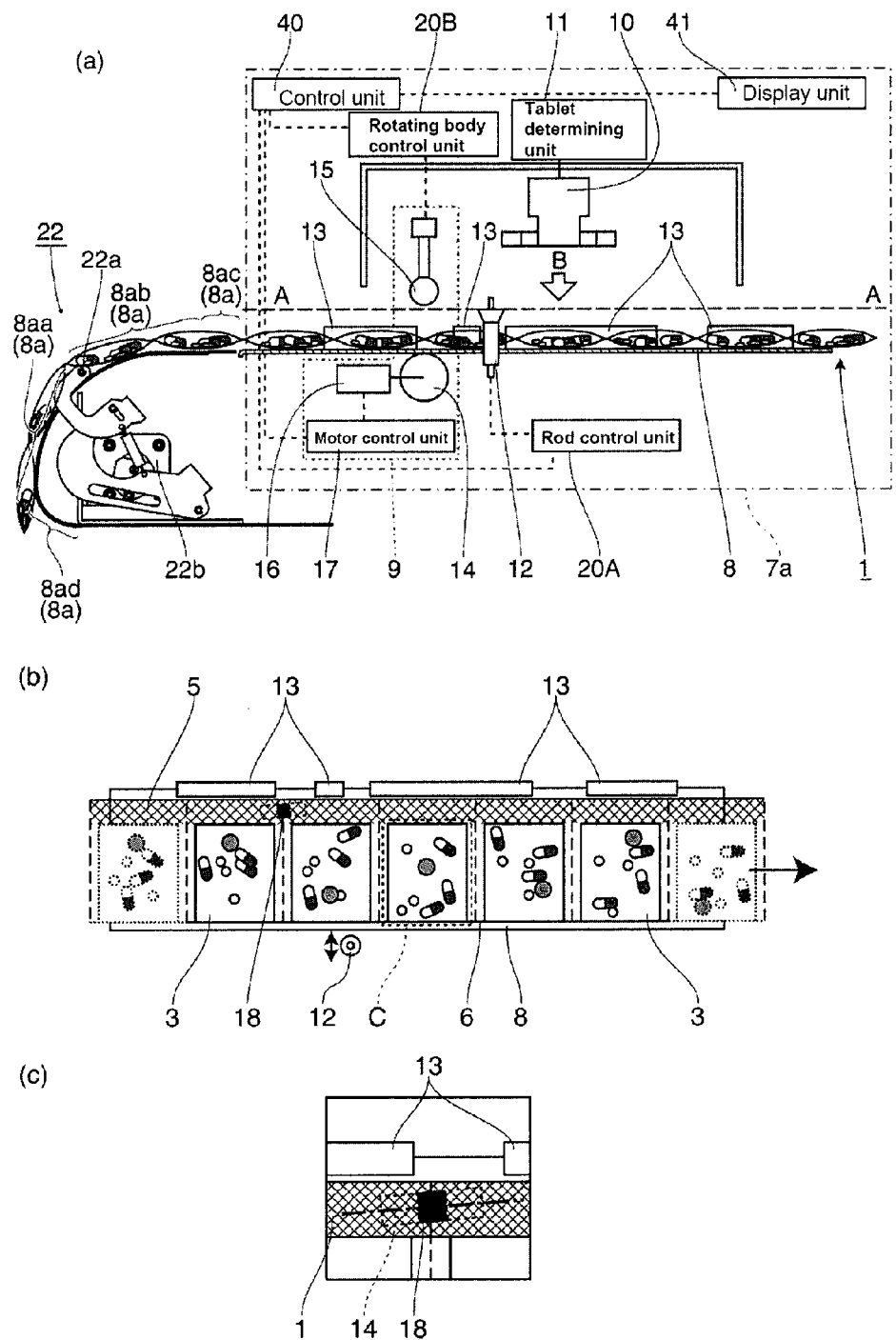
FIG. 2(a) is a partial sectional side view showing an outline configuration of a tablet-inspecting device in a first embodiment of the invention.
FIG. 2(b) is a plan view of a surface A-A in FIG. 2(a) as viewed from an arrow B (from above)
FIG. 2(c) is an enlarged view of essential portions in FIG. 2(b)

The rod unit 12 is operated by the rod control unit 20A, and the rod control unit 20A is operated by the operation instructions from the control unit 40 (FIG. 2).

As shown in FIGS. 3(a) and 4(a), the rod unit 12 is disposed at a predetermined distance from the continuous drug packet 1.

If the operation instructions are given from the control unit 40, the rod unit 12 is operated by the rod control unit 20A, and the rod unit 12 presses the continuous drug packet 1 as shown in FIGS. 3(b) and 4(b).

The rod unit 12 presses the folded back portion 6 of the continuous drug packet 1. By the pressing operation of the rod unit 12, the height of the drug packet 3 can be increased.

A symbol F in FIG. 4(a) shows the height of the drug packet 3 in a state where the drug packet 3 is not pressed by the rod unit 12, and a symbol G in FIG. 4(b) shows the height of the drug packet 3 in a state where the drug packet 3 is pressed by the rod unit 12. The height G is higher than the height F and as a result, a space 19 in the drug packet 3 can be widened.

When the rod unit 12 is pressed against the clamped portion 5, since the clamped portion 5 is formed by clamping and is hard, the clamped portion 5 is not easily deformed, the space 19 in the drug packet 3 is not easily widened, and there is a possibility that the drug packet 3 is broken. However, according to the tablet-inspecting device 7a of the embodiment, if the rod unit 12 is pressed against the folded back portion 6, the space 19 in the drug packet 3 can be widened and moving amounts of the tablets 2 in the drug packet 3 can be increased.

Therefore, according to the tablet-inspecting device 7a of the embodiment, the moving amounts of the tablets 2 in the drug packet 3 can be increased by reciprocating the continuous drug packet 1, and a dispersion effect of the tablets 2 can be enhanced.

As shown in FIG. 4, the rod unit 12 is provided with a columnar first rotating unit 12a which can rotate with respect to a shaft H. Since the first rotating unit 12a is in contact with the drug packet 3 during the reciprocating operation of the continuous drug packet 1, the first rotating unit 12a is rotated by the reciprocating operation of the drug packet 3. Since the first rotating unit 12a rotates in tandem with the reciprocating operation of the drug packet 3, it is possible to prevent the drug packet 3, i.e., the continuous drug packet 1 from being broken.

An upper portion of the first rotating unit 12a is provided with a truncated conical second rotating unit 12b which can rotate with respect to the shaft H. The second rotating unit 12b rotates in tandem with the reciprocating operation of the continuous drug packet 1 together with the first rotating unit 12a. The second rotating unit 12b may be rotated by contact with the drug packet 3.

When the rod unit 12 is pressed against the folded back portion 6, an upper surface of the drug packet 3 largely rises in some cases depending upon a state of the continuous drug packet 1 and the drug packet 3, e.g., depending upon an uneven positions of the tablets 2 in the drug packet 3. If the upper surface of the drug packet 3 excessively largely rises, the drug packet 3 is broken in some cases. In this embodiment, by providing the second rotating unit 12b, the upper surface of the drug packet 3 is prevented from rising when the rod unit 12 is pressed against the folded back portion 6.

After the pressing operation of the rod, the continuous drug packet 1 is reciprocated.

The reciprocating operation of the continuous drug packet will be described below.

FIG. 5(a) is a plan view before the tablet-inspecting device in the first embodiment of the invention reciprocates, FIG. 5(b) is a plan view after the tablet-inspecting device moved forward, and FIG. 5(c) is a plan view after the tablet-inspecting device moved backward.

FIG. 6(a) is a plan view showing drugs in the drug packet before the tablet-inspecting device in the first embodiment of the invention reciprocates, FIG. 6(b) is a plan view showing drugs in the drug packet after the tablet-inspecting device moved forward, and FIG. 6(c) is a plan view showing drugs in the drug packet after the tablet-inspecting device moved backward.

This reciprocating operation is achieved by alternately carrying out the forward operation for moving the continuous drug packet 1 toward the downstream side of the conveyor path 8, and the backward operation for moving the continuous drug packet 1 toward the upstream side of the conveyor path 8. The forward operation and the backward operation are carried out by reversing the rotation direction with respect to the motor unit 16.

The reciprocating operation of the continuous drug packet 1 is carried out by instructions of reciprocating operation from the control unit 40 with respect to the motor control unit 17. The continuous drug packet 1 is operated by turning motion of the first rotating body 14. The first rotating body 14 is turned by the motor unit 16. The turning motion of the motor unit 16 is controlled by the motor control unit 17.

In a state where the rod unit 12 is pressed against a side portion of the drug packet 3, the continuous drug packet 1 is moved forward by the continuous drug packet-driving unit 9.

By this forward operation, the continuous drug packet 1 moves from a state shown in FIG. 5(a) to a state shown in FIG. 5(b), and from a state shown in FIG. 6(a) to a state shown in FIG. 6(b). That is, the continuous drug packet 1 moves from the upstream side to the downstream side of the conveyor path 8 by a distance E.

After this forward operation, in the state where the rod unit 12 is pressed against the side portion of the drug packet 3, the continuous drug packet 1 is moved backward by the continuous drug packet-driving unit 9.

By this backward operation, the continuous drug packet 1 moves from a state shown in FIG. 5(b) to a state shown in FIG. 5(c), and from a state shown in FIG. 6(b) to a state shown in FIG. 6(c). That is, the continuous drug packet 1 moves from the downstream side to the upstream side of the conveyor path 8 by the distance E.

After this backward operation, the forward operation is again carried out, and the reciprocating operations are carried out preset times.

Figure 6:
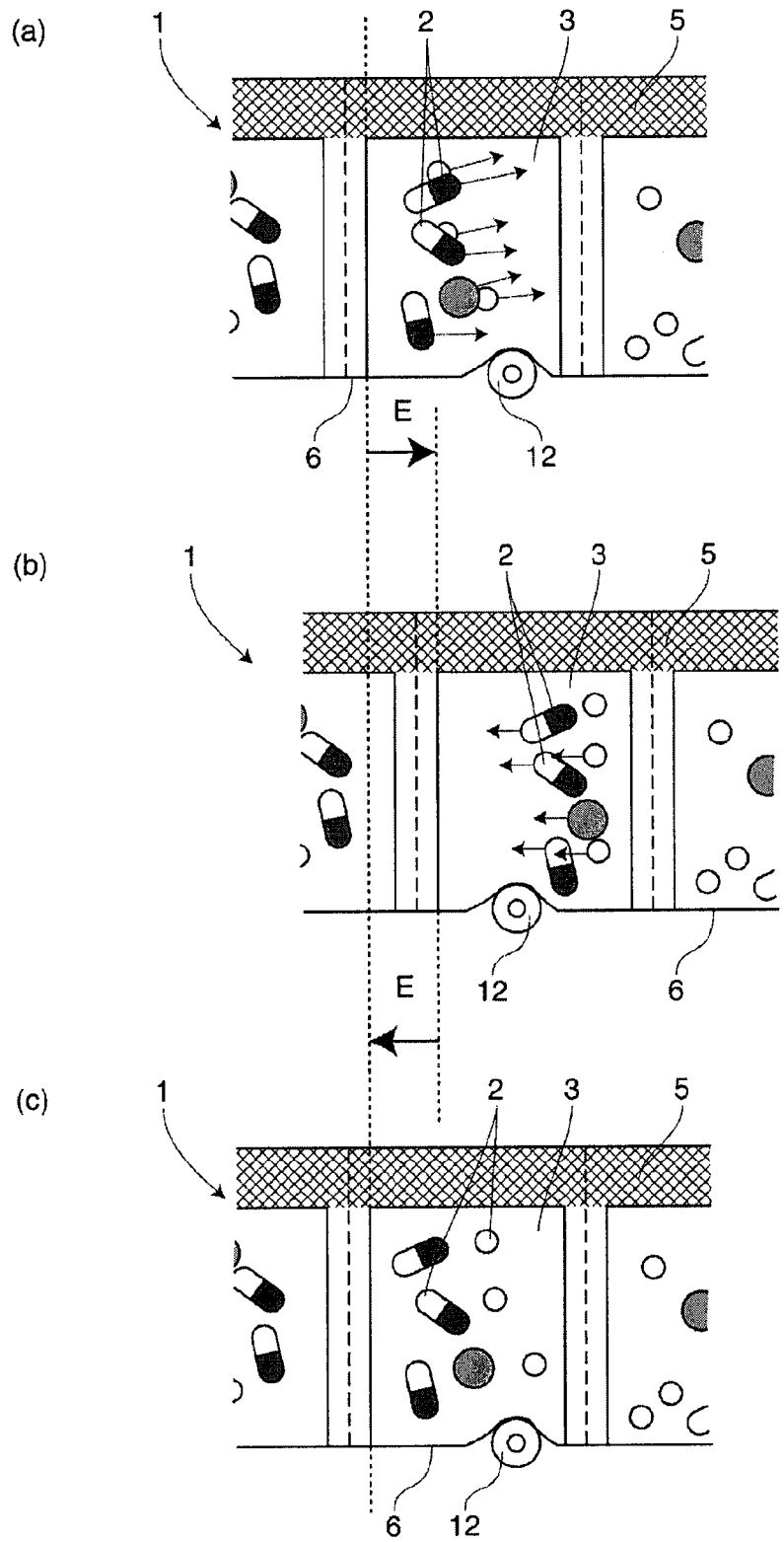
FIG. 6 are plan views showing drugs in a drug packet in the reciprocating operation of the tablet-inspecting device.

An effect obtained by the reciprocating operation of the continuous drug packet 1 will be described using FIG. 6.

As shown in FIG. 6(a), the continuous drug packet 1 moves forward by the distance E. According to this, tablets 2 in the drug packet 3 move to the downstream side (rightward in FIG. 6(a)).

After this forward operation, the continuous drug packet 1 moves backward by the distance E. According to this, the tablets 2 in the drug packet 3 move to the upstream side (leftward in FIG. 6(b)).

In this embodiment, the distance E was 5 mm, and an excellent result could be obtained.

According to this embodiment, the rod unit 12 is pressed against the side portion of the drug packet 3, and the space in the drug packet 3 is widened. By reciprocating the continuous drug packet 1, tablets 2 in the drug packet 3 can move by a relatively long distance with respect to a size of the tablet 2, e.g., by a distance of about the size of the tablet 2 to about several times of the size of the tablet 2. The movement of the tablets 2 promotes collision between the tablets 2 in the drug packet 3, and the tablets 2 are dispersed in the drug packet 3.

Even if stop time of one second or longer is provided between the forward operation and the backward operation, the same effect can be obtained.

After the reciprocating operation of the continuous drug packet 1, separating operation of the rod unit 12 is carried out.

The separating operation of the rod unit 12 will be described with reference to FIGS. 3 and 4.

The rod unit 12 is operated by the rod control unit 20A. The rod control unit 20A is operated by the operation instructions from the control unit 40.

As shown in FIGS. 3(b) and 4(b), in the reciprocating operation of the continuous drug packet 1, the rod unit 12 is in the state where it is pressed against the continuous drug packet 1.

If the operation instructions are given from the control unit 40, the rod unit 12 is operated by the rod control unit 20A and as shown in FIGS. 3(a) and 4(c), the rod unit 12 separates from the continuous drug packet 1.

If the drug packet-sending operation is carried out in the state where the rod unit 12 is pressed against the side portion of the drug packet 3, the continuous drug packet 1, i.e., the drug packet 3 is broken during the drug packet-sending operation. In this embodiment, by separating the rod unit 12 from the side portion of the drug packet 3 by the separating operation of the rod unit 12, it is possible to prevent the continuous drug packet 1, i.e., the drug packet 3 from being broken.

After the separating operation of the rod unit 12, the drug packet-sending operation is carried out.

The drug packet-sending operation will be described below.

FIG. 7(a) is a plan view before the drug packet-sending operation of the tablet-inspecting device in the first embodiment of the invention is carried out, and FIG. 7(b) is a plan view after the drug packet-sending operation of the tablet-inspecting device was carried out.

In FIG. 7, a symbol N indicates an N-th drug packet 3, a symbol N+1 indicates a drug packet 3 located upstream of the N-th drug packet 3, and a symbol N−1 indicates a drug packet 3 located downstream of the N-th drug packet 3.

The drug packet-sending operation is carried out by moving, by a distance J, the continuous drug packet 1 to the downstream side of the conveyor path 8 by the continuous drug packet-driving unit 9.

The drug packet-sending operation of the continuous drug packet 1 is carried out by operation instructions from the control unit 40 with respect to the motor control unit 17. The continuous drug packet 1 is operated by turning motion of the first rotating body 14. The first rotating body 14 is turned by the motor unit 16. The turning motion of the motor unit 16 is controlled by the motor control unit 17.

As shown in FIG. 7(b), the N-th drug packet 3 in FIG. 7(a) is moved by the drug packet-sending operation to a region C where the imaging unit 10 takes an image. The distance J corresponds to a length of the drug packet 3 in the continuous drug packet 1 in the longitudinal direction.

After the drug packet-sending operation, an image-taking operation and a tablet-inspecting operation are carried out.

The image-taking operation and the tablet-inspecting operation will be described below.

The tablet-inspecting operation includes a inspecting operation for inspecting the number of tablets and inspecting operation for inspecting kinds of tablets but here, a counting operation for counting the number of tablets will be described as the tablet-inspecting operation.

During the N-th drug packet 3, tablets 2 in the N-th drug packet 3 are dispersed. This N-th drug packet 3 moves to the region C where the imaging unit 10 takes an image shown in FIG. 2.

In this state, the imaging unit 10 takes an image of the N-th drug packet 3. The shoot image of the N-th tablet 2 is sent to the tablet determining unit 11 shown in FIG. 2. The tablet determining unit 11 counts the number of tablets 2 in the drug packet 3 based on the image of the tablet 2 taken by the imaging unit 10.

If the image-taking operation of the N-th drug packet 3 is completed, the following operations are carried out for the N+1-th drug packet 3. That is, a pressing operation of the rod unit 12, a reciprocating operation of the continuous drug packet 1, a separating operation of the rod unit 12, a sending operation and an image-taking operation of the drug packet 3 are carried out.

As described above, for each of the drug packets 3, the tablet-inspecting device 7a repeatedly carries out the pressing operation of the rod unit 12, the reciprocating operation of the continuous drug packet 1, the separating operation of the rod unit 12, and the sending operation, the image-taking operation and the tablet-inspecting operation of the drug packet 3. According to this, it is possible to stably inspect drugs in each of the drug packets 3 in the continuous drug packet 1.

Figure 8:
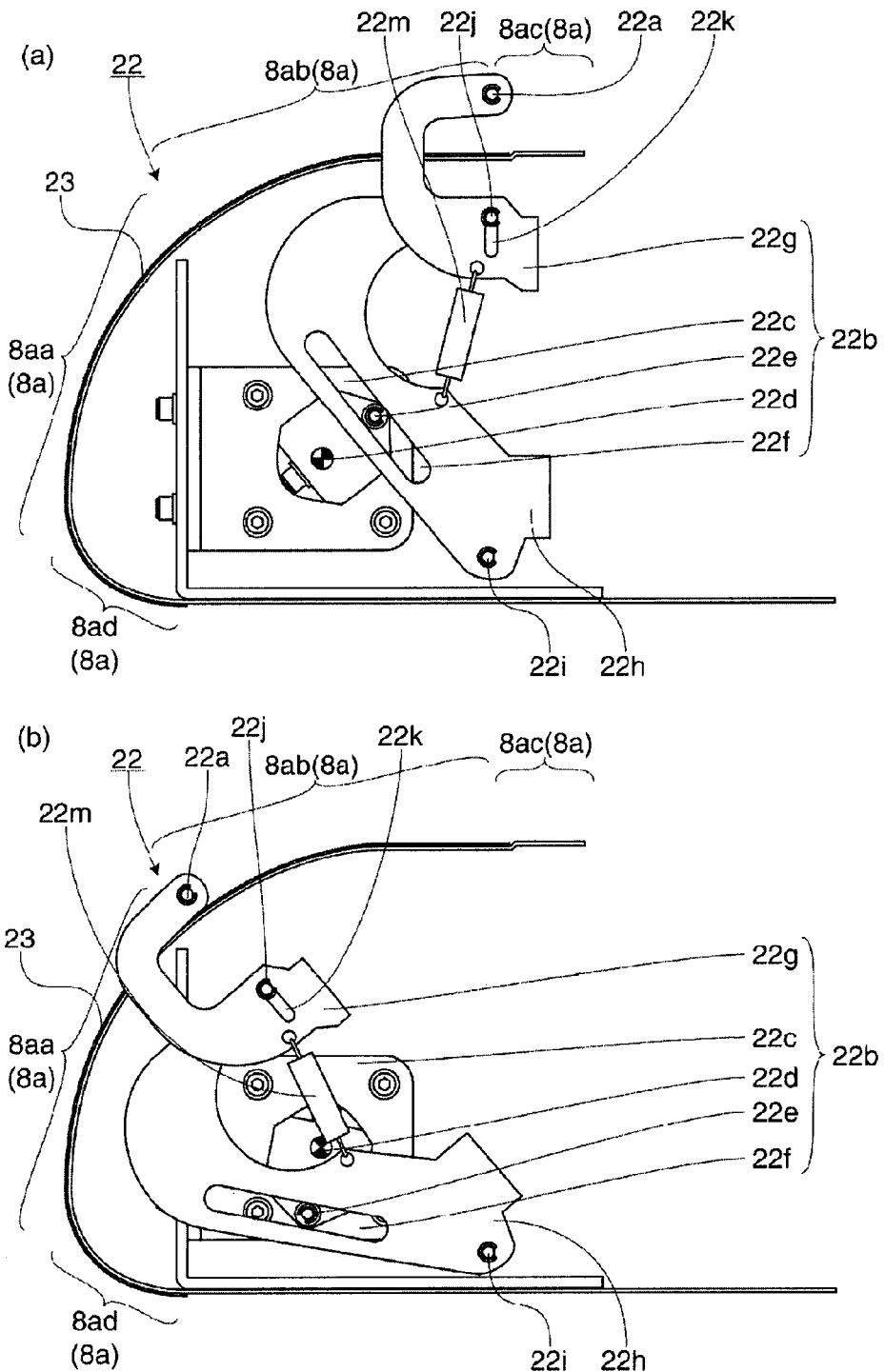
FIG. 8 are side views showing second tablet separating means of the tablet-inspecting device.

Next, the second tablet separating means 22 of the tablet-inspecting device of the embodiment will be described using FIG. 8.

The driving unit 22b includes a motor 22c, an eccentric shaft 22e provided at a position eccentric from a rotation shaft 22d of the motor 22c, a cam groove 22f which is linked to the eccentric shaft 22e, and a support member 22g which reciprocates in a predetermined range by the cam groove 22f.

The cam groove 22f is formed in a swinging arm 22h. A fulcrum 22i is provided on one end of the swinging arm 22h, and the swinging arm 22h swings around the fulcrum 22i within a predetermined range. The other end of the swinging arm 22h is provided with a pin 22j which holds the support member 22g.

The support member 22g is provided with a long hole 22k which is linked to the pin 22j.

The pin 22j is biased toward one end of the long hole 22k by tension of a spring 22m. One end of the spring 22m is connected to the other end of the long hole 22k, the other end of the spring 22m is connected to the swinging arm 22h, and tension is always applied in a tensile direction.

The rod 22a is provided on the support member 22g. It is preferable that the rod 22a is provided such that it can turn with respect to the support member 22g. It is preferable that a diameter of the rod 22a is smaller than a length (distance J) of the drug packet 3 in the continuous drug packet 1 in the longitudinal direction.

A vibration isolating material 23 made of sponge or rubber is pasted on an upper surface of the introduction path 8a. It is preferable that the vibration isolating material 23 is provided at least in the introduction path 8aa.

An operation of the second tablet separating means 22 will be described below.

The rod 22a of the second tablet separating means 22 swings within a range of the introduction path 8ab by the rotation of the motor 22c.

The eccentric shaft 22e turns around the rotation shaft 22d by the rotation of the motor 22c at a predetermined distance from the rotation shaft 22d.

The swinging arm 22h receives a force by turning motion of the eccentric shaft 22e, and the swinging arm 22h swings around the fulcrum 22i within a predetermined range. The eccentric shaft 22e moves in the cam groove 22f.

By the swinging operation of the swinging arm 22h around the fulcrum 22i, the support member 22g alternately moves to the upstream side and the downstream side of the introduction path 8.

Therefore, the rod 22a swings by the movement of the support member 22g within the range of the introduction path 8ab.

According to the embodiment, the rod 22a reciprocates on the lower surface of the continuous drug packet 1. According to this, it is possible to disperse the tablets 2.

According to this embodiment, the rod 22a is provided such that it can turn with respect to the support member 22g. According to this, printed information of the continuous drug packet 1 is not erased.

According to this embodiment, since the swinging arm 22h and the support member 22g are connected to each other through the long hole 22k, if an unplanned load is applied, the support member 22g can displace by a length of the long hole 22k. Therefore, when a foreign matter is sandwiched between the introduction path 8 and the rod 22a during the operation of the second tablet separating means 22, the support member 22g is displaced and safety can be secured.

According to this embodiment, the vibration isolating material 23 is provided at least in the introduction path 8aa. According to this, it is possible to avoid a case in which the continuous drug packet 1 which hangs down by its own weight collides against the introduction path 8aa by the swinging operation of the rod 22a and a noise is generated.

As described above, According to the tablet-inspecting device 7a of the embodiment, it is possible to widen the space in the drug packet 3 by pressing the rod unit 12 against the side portion of the drug packet 3. According to the tablet-inspecting device 7a, the reciprocating operation is carried in the moving direction of the continuous drug packet 1 in the state where the space in the drug packet 3 is widened. According to this, tablets 2 can be dispersed in the drug packet 3. Therefore, according to the tablet-inspecting device 7a, it is possible to prevent tablets 2 from concentrating on one region in the drug packet 3, and it is possible to stably count the number of drugs.

In this embodiment, the rod unit 12 is provided with the columnar first rotating unit 12a which can rotate with respect to the shaft H as shown in FIG. 4. Since the first rotating unit 12a rotates in tandem with the reciprocating operation of the continuous drug packet 1, it is possible to prevent the continuous drug packet 1 from being broken.

In this embodiment, the upper portion of the first rotating unit 12a of the rod unit 12 is provided with the truncated conical second rotating unit 12b which can rotate with respect to the shaft H as shown in FIG. 4. This second rotating unit 12b can prevent the drug packet 3 from being broken by the large rising motion of the upper surface of the drug packet 3.

(Second Embodiment)

Next, a tablet-inspecting device in a second embodiment will be described.

FIG. 9(a) is a partial sectional side view showing an outline configuration of the tablet-inspecting device in the second embodiment of the invention, and FIG. 9(b) is a plan view of a surface A-A in FIG. 9(a) as viewed from an arrow B (from above). The same symbols are allocated to the same members as those of the first embodiment, and explanation thereof will be omitted.

A tablet-inspecting device 7b in the second embodiment includes a drive-assisting unit 24 located more downstream of the conveyor path 8 than the imaging unit 10. The drive-assisting unit 24 is composed of a third rotating body 24a disposed on a lower portion of the conveyor path 8, and a fourth rotating body 24b disposed on an upper portion of the conveyor path 8.

The third rotating body 24a and the fourth rotating body 24b are disposed at positions of the clamped portion 5. The third rotating body 24a and the fourth rotating body 24b sandwich a second contact portion 29 on the clamped portion 5 of the continuous drug packet 1.

The third rotating body 24a rotates such that it pushes up the clamped portion 5 of the continuous drug packet 1 from its lower surface. The fourth rotating body 24b rotates by pushing the clamped portion 5 of the continuous drug packet 1 from its upper surface.

A first gear portion 25a is provided on the first rotating body 14 of the continuous drug packet-driving unit 9. A second gear portion 25b is provided on the third rotating body 24a of the drive-assisting unit 24. The first gear portion 25a and the second gear portion 25b are connected to each other through a belt 25c. The continuous drug packet-driving unit 9 and the drive-assisting unit 24 move in tandem with each other.

If the drive-assisting unit 24 is provided more downstream of the conveyor path 8 than the imaging unit 10 as in the second embodiment, it is possible to more reliably maintain the position of the continuous drug packet 1 in the imaging unit 10.

Concerning the third rotating body 24a and the fourth rotating body 24b also, their rotation shafts may be provided such that a discharging direction discharged by the third rotating body 24a or a discharging direction discharged by the fourth rotating body 24b becomes a direction approaching the guide 13.

(Third Embodiment)

Next, a tablet-inspecting device in a third embodiment will be described.

Figure 10:
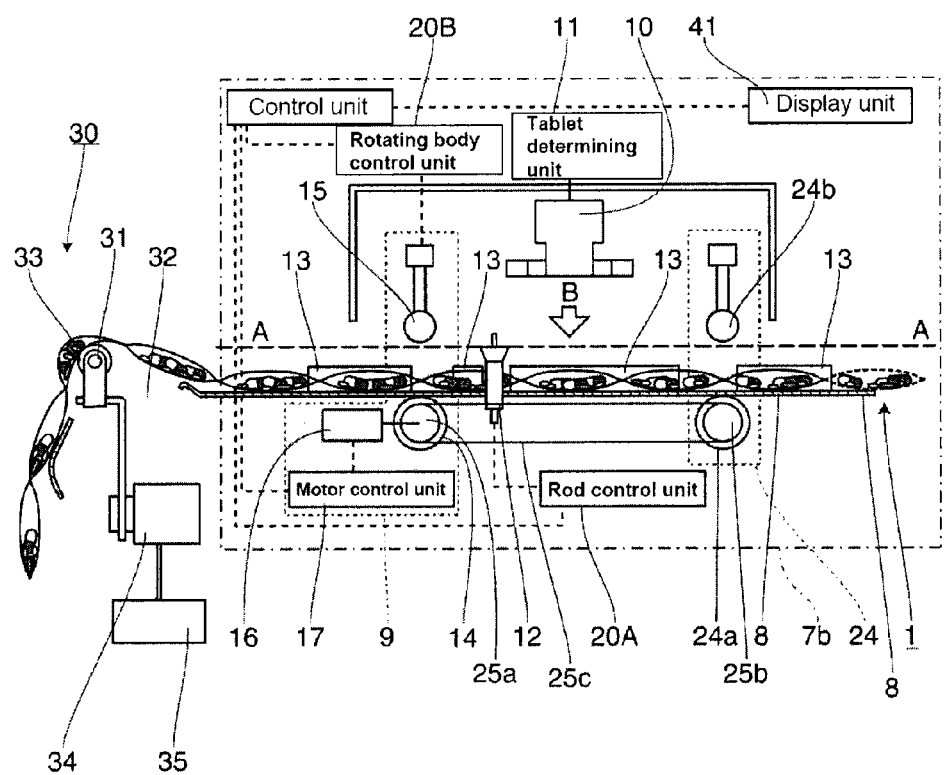
FIG. 10 is a partial sectional side view showing an outline configuration of a tablet-inspecting device in a third embodiment of the invention.
Figure 11:
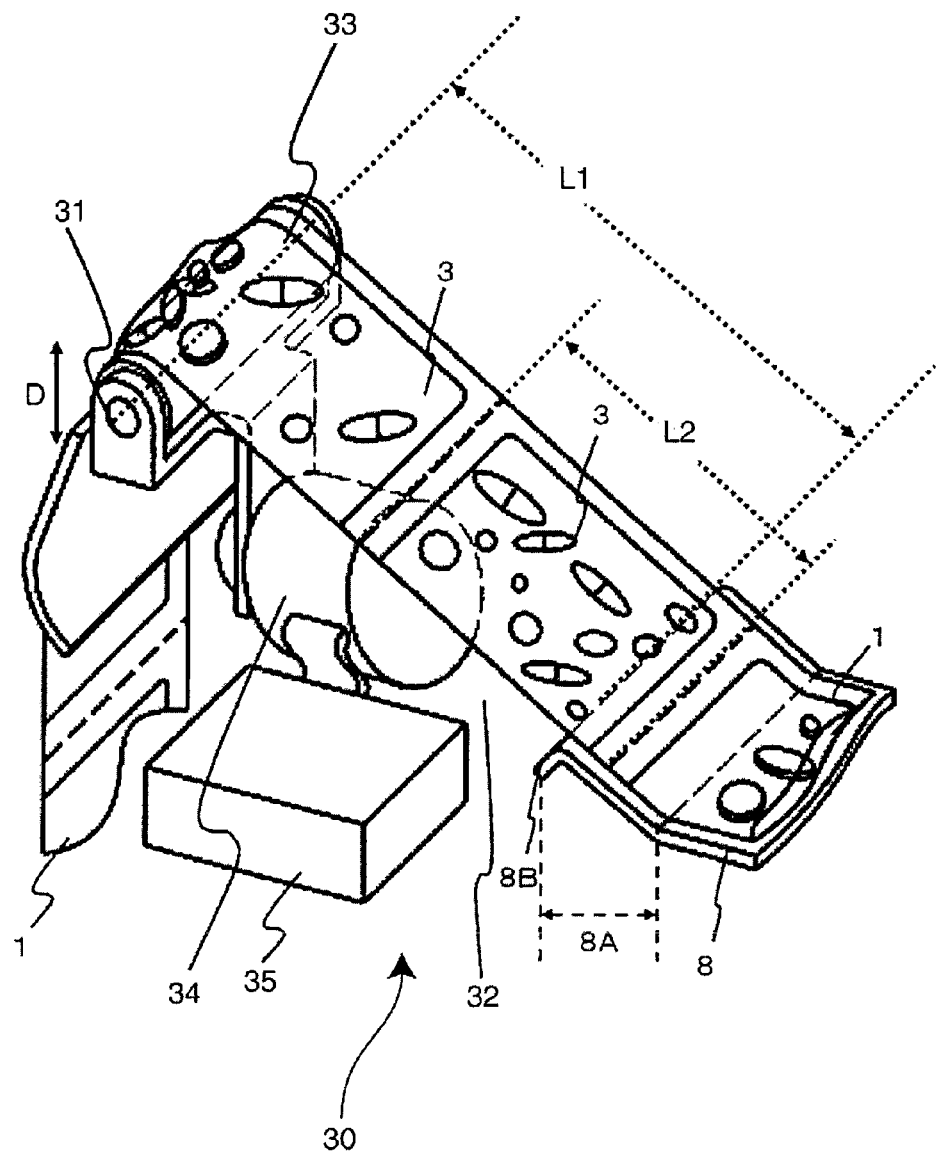
FIG. 11 is a perspective view of essential portions of the tablet-inspecting device.

FIG. 10 is a partial sectional side view showing an outline configuration of the tablet-inspecting device in the third embodiment of the invention, and FIG. 11 is a perspective view of essential portions of the tablet-inspecting device. The same symbols are allocated to the same members as those of the above-described embodiment, and explanation thereof will be omitted.

In the third embodiment, a third tablet separating means 30 is provided instead of the second tablet separating means 22 of the first embodiment.

A tablet-inspecting device 7c of the third embodiment includes the third tablet separating means 30.

The third tablet separating means 30 of the third embodiment includes vibrating means 31 disposed above the conveyor path 8 and a vibration space 32 provided between the vibrating means 31 and the conveyor path 8 on an upstream side 8A of the conveyor path 8.

The vibrating means 31 of the third embodiment is composed of a roller 33 which rotates in a travelling direction of the continuous drug packet 1. The continuous drug packet 1 is placed on an outer surface of the roller 33. The vibrating means 31 is also composed of a vibration motor 34 which vibrates the roller 33, and a vibration motor control unit 35 which controls the vibration motor 34.

According to this configuration, the continuous drug packet 1 placed on the roller 33 can be vibrated in a vertical direction (arrow D in FIG. 11) by the vibration motor 34.

A length (L1 in FIG. 11) of the vibration space 32 of the embodiment from the vibrating means 31 to the conveyor path 8 is set longer than a length (L2 in FIG. 11) of the drug packet 3 in the conveying direction.

In the third embodiment, the continuous drug packet 1 is disposed such that it is supplied toward the upper side roller 33 from a lower side of the upstream side of the roller 33.

In the third embodiment, the upstream side 8A of the conveyor path 8 tilts upward toward the third tablet separating means 30. According to this configuration, it is possible to more reliably separate, from one another, the tablets 2 in the drug packet 3 of the continuous drug packet 1.

In the third embodiment, an upstream end 8B of the conveyor path 8 tilts downward. According to this configuration, it is possible to reduce damage on an outer surface of the drug packet 3 which may adversely be generated when a later-described operation (tablet separating operation, hereinafter) for separating, from one another, the tablets 2 in the drug packet 3 of the continuous drug packet 1 of the embodiment.

Next, the tablet separating operation of the third embodiment will be described.

Figure 12:
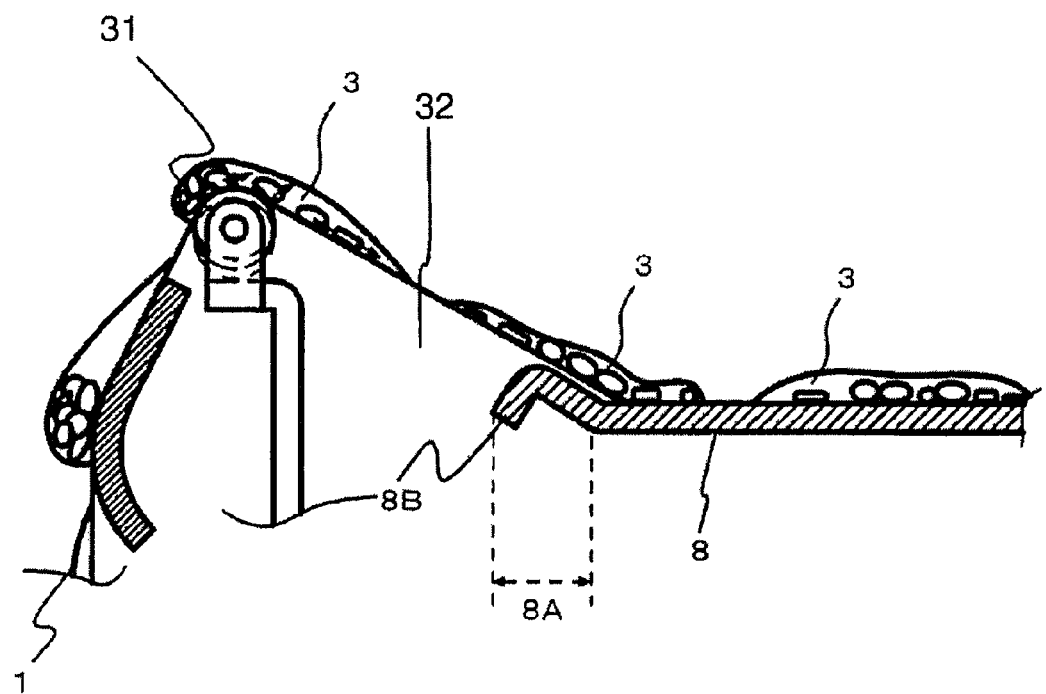
FIG. 12 is an enlarged sectional view of essential portions of a non-vibrated state in the tablet-inspecting device.
Figure 13:
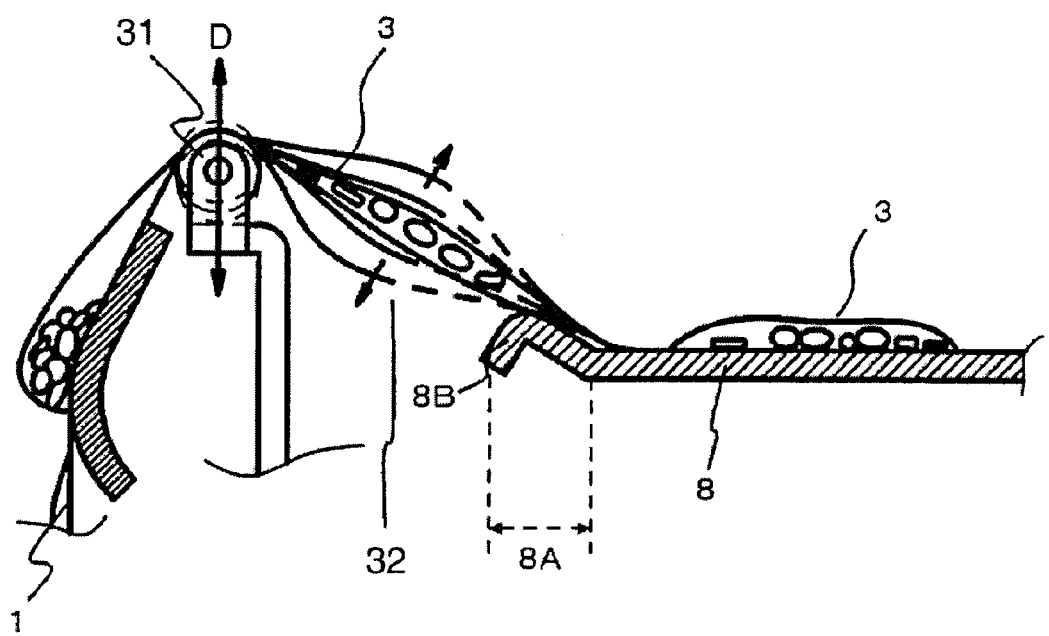
FIG. 13 is an enlarged sectional view of essential portions of a vibrated state in the tablet-inspecting device.
Figure 14:
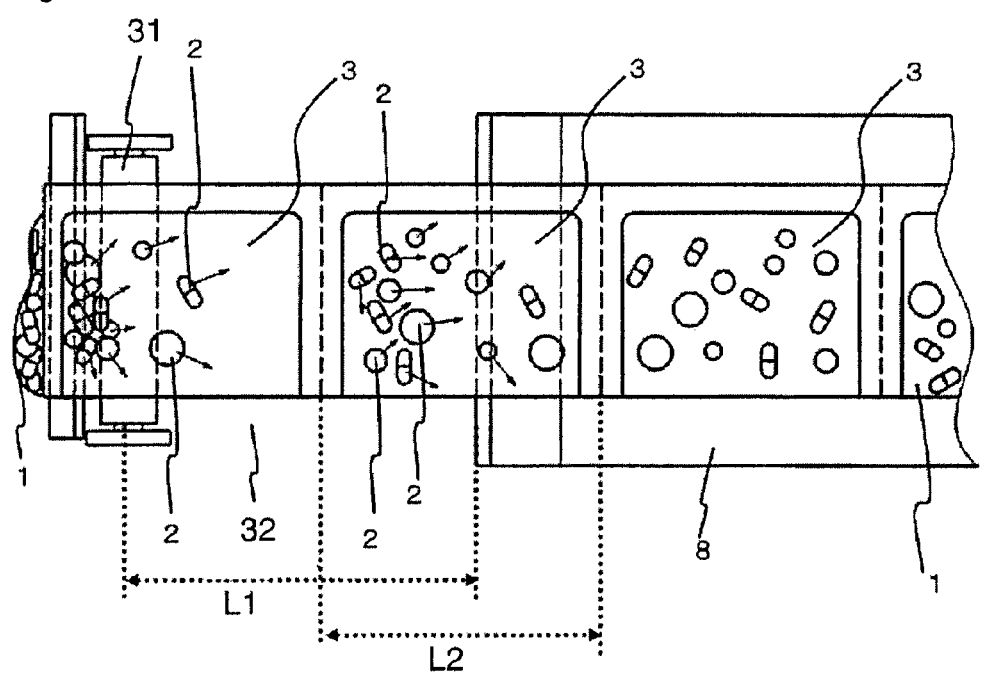
FIG. 14 is a plan view for explaining a tablet separating operation in the tablet-inspecting device.

FIG. 12 is an enlarged sectional view of essential portions of a non-vibrated state in the tablet-inspecting device of the third embodiment, FIG. 13 is an enlarged sectional view of essential portions of a vibrated state in the tablet-inspecting device, and FIG. 14 is a plan view for explaining the tablet separating operation in the tablet-inspecting device.

As shown in FIG. 13, the roller 33 of the vibrating means 31 vibrates in the vertical direction (direction intersecting with travelling direction) D and according to this, the drug packet 3 is vibrated.

The vibrated drug packet 3 is largely vibrated in the vertical direction (direction perpendicular to the outer surface of the continuous drug packet 1) in the next vibration space 32. As a result, the plurality of tablets 2 included in the drug packet 3 are appropriately separated from one another as shown in FIG. 13. According to this, it is possible to enhance the counting precision of the tablet counting operation of the tablet determining unit 11 which is conducted on the downstream side.

In the third embodiment, the upstream side 8A of the conveyor path 8 tilts upward toward a tablet separating means 30.

That is, since the third tablet separating means 30 downwardly tilts toward the upstream end BE of the conveyor path 8 from the roller 33. Therefore, when the third tablet separating means 30 largely swings in the vertical direction in the vibration space 32, the tablets 2 can more largely be separated from one another by their own weights, and this configuration can further enhance the counting precision of the tablet counting operation of the tablet determining unit 11 which is conducted on the downstream side.

In the third embodiment, since the upstream end 8B of the conveyor path 8 tilts downward, when the continuous drug packet 1 largely swings in the vertical direction in the vibration space 32, it is possible to reduce an impact received when the upstream end 8B of the conveyor path 8 strikes the continuous drug packet 1 and according to this, it is possible to reduce damage on the outer surface of the drug packet 3.

Although the vibrating means 31 is vibrated by the vibration motor 34 in the vertical direction in the third embodiment, the drug packet 3 can largely be vibrated in the vibration space 32 even if the vibrating means 31 is vibrated in the lateral direction or the oblique direction.

(Fourth Embodiment)

Next, a tablet-inspecting device 7d in a fourth embodiment will be described.

Figure 15:
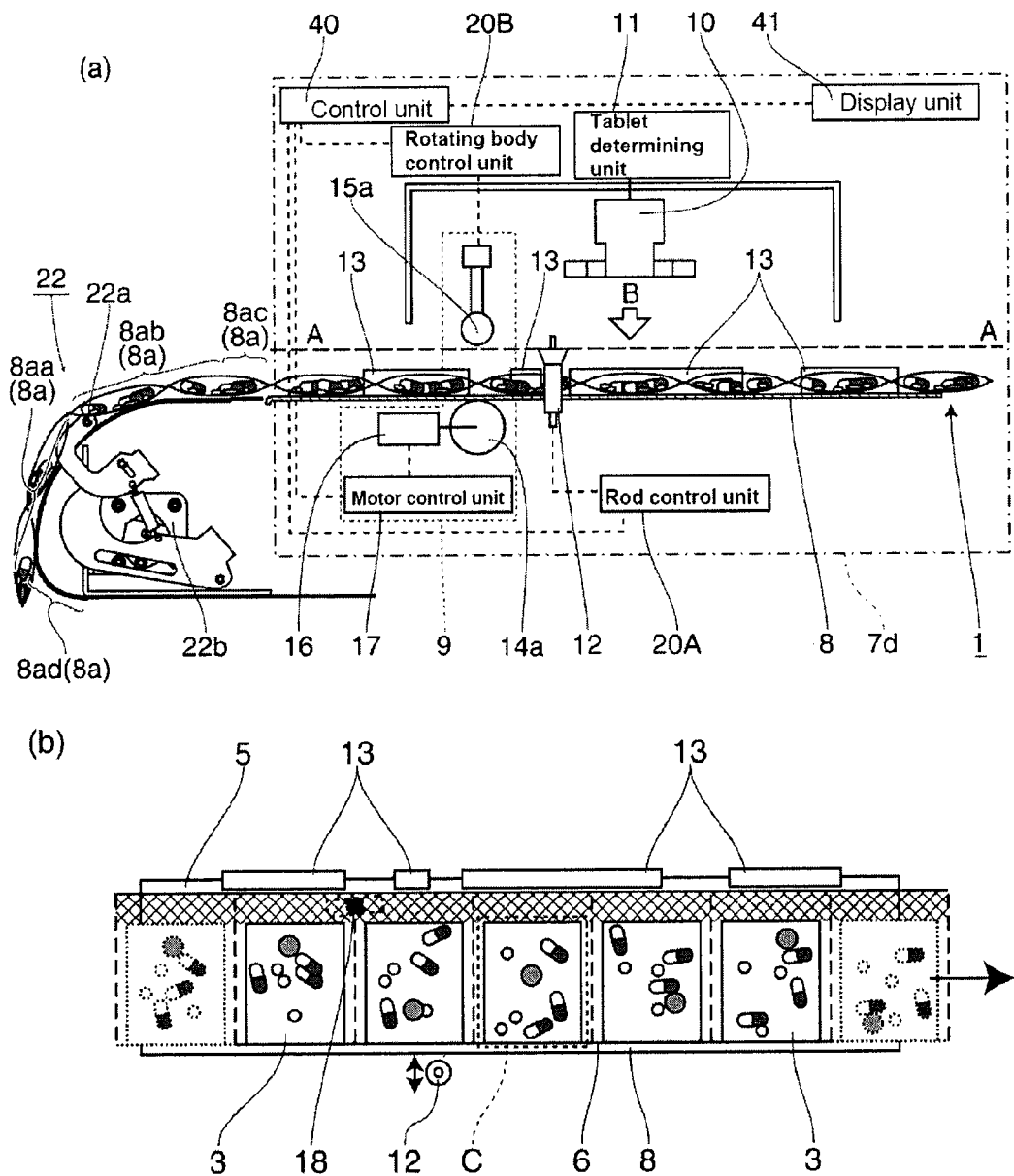
FIG. 15(a) is a partial sectional side view showing an outline configuration of a tablet-inspecting device in a fourth embodiment of the invention.
FIG. 15(b) is a plan view of a surface A-A in FIG. 15(a) as viewed from an arrow B (from above)

FIG. 15(a) is a partial sectional side view showing an outline configuration of the tablet-inspecting device in the fourth embodiment, and FIG. 15(b) is a plan view of a surface A-A in FIG. 15(a) as viewed from an arrow B (from above). The same symbols are allocated to the same members as those of the above-described embodiment, and explanation thereof will be omitted.

In the fourth embodiment, a continuous drug packet-driving unit 9 includes a first rotating body 14a disposed on a lower portion of a conveyor path 8, a second rotating body 15a disposed on an upper portion of the conveyor path 8, a motor unit 16 connected to the first rotating body 14a, and a motor control unit 17 which controls the motor unit 16.

At least a surface of the first rotating body 14a which becomes a contact portion 18 is made of rubber, and at least a surface of the second rotating body 15a which becomes the contact portion 18 is made of plastic.

The first rotating body 14a and the second rotating body 15a are disposed at positions of the clamped portion 5.

The first rotating body 14a rotates such that is pushes up the clamped portion 5 of the continuous drug packet 1 from its lower surface. The second rotating body 15a presses the clamped portion 5 of the continuous drug packet 1 from its upper surface and according to this, the second rotating body 15a rotates.

In the fourth embodiment also, a rotation shaft of the first rotating body 14a or the second rotating body 15a may be provided such that a discharging direction discharged by the first rotating body 14a or the second rotating body 15a becomes a direction approaching the guide 13 as in the first embodiment.

FIG. 16(a) is a plan view showing a state where a conveying direction of a drug continuous body is deviated in the tablet-inspecting device 7d of the fourth embodiment, and FIG. 16(b) is a plan view showing a state after the continuous drug packet comes into contact with the guide.

As shown in FIG. 16(a) for example, the drug continuous body is deviated toward one side with respect to a conveying direction of the continuous drug packet 1 in some cases. If the continuous drug packet 1 is continued to be conveyed in the deviated direction even after the continuous drug packet 1 comes into contact with the guide 13, the continuous drug packet 1 is broken or the conveyor path 8 is clogged with the continuous drug packet 1.

However, in the continuous drug packet-driving unit 9 of the fourth embodiment, when a throwing direction or the conveying direction of the continuous drug packet 1 is deviated, although the continuous drug packet 1 comes into contact with the guide 13, since the second rotating body 15a is made of plastic and a friction coefficient between the second rotating body 15a and the continuous drug packet 1 is small, "slips" is temporality generated between the rotating body 15a and the continuous drug packet 1, and the conveying direction of the continuous drug packet 1 is corrected to a desired direction by this "slips". Therefore, the continuous drug packet 1 returns to the original conveying direction of the conveyor path 8 as shown in FIG. 16(b), and inconvenience which may be caused when the continuous drug packet 1 moves in the state where it is deviated toward one side is not generated. Here, a longitudinal direction of the continuous drug packet 1 is the conveying direction of the conveyor path 8.

If the guides 13 are provided on both sides of the conveyor path 8, even if the continuous drug packet 1 is deviated to the other side from the conveying direction of the continuous drug packet 1, since the second rotating body 15a is made of plastic, "slip" is temporarily generated between the rotating body 15a and the continuous drug packet 1 and as a result, the conveying direction of the continuous drug packet 1 is corrected to a desired direction.

(Fifth Embodiment)

Next, a tablet-inspecting device in a fifth embodiment will be described.

Figure 17:
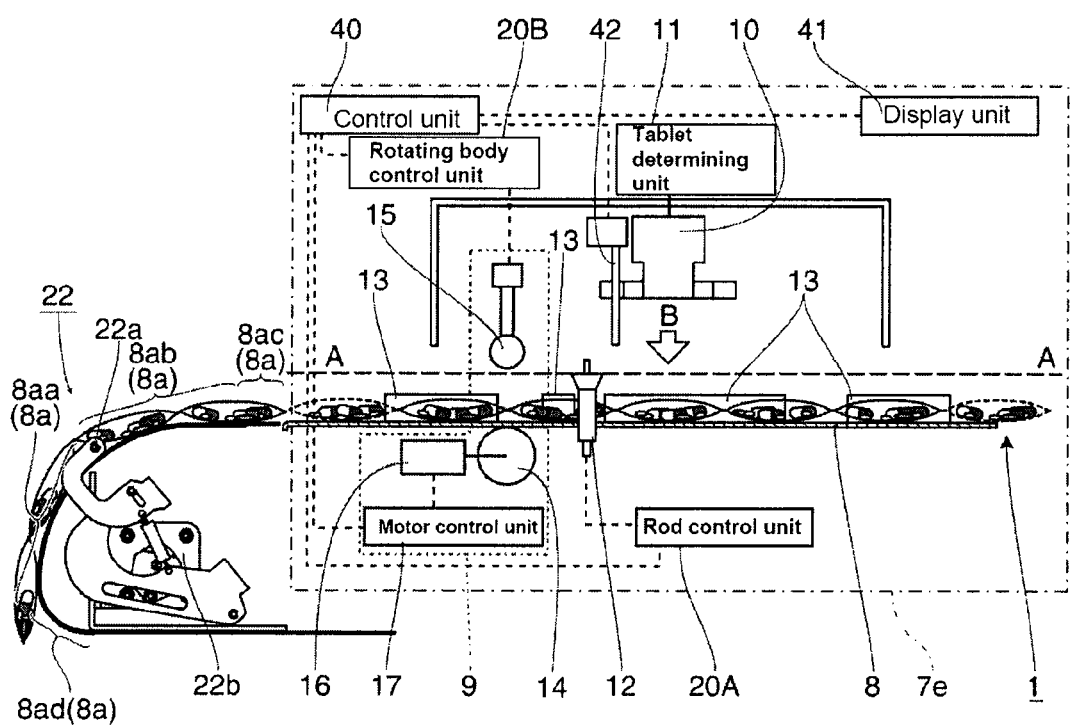
FIG. 17 is a partial sectional side view showing an outline configuration of a tablet-inspecting device in a fifth embodiment of the invention.

FIG. 17 is a partial sectional side view showing an outline configuration of the tablet-inspecting device in the fifth embodiment. The same symbols are allocated to the same members as those of the above-described embodiment, and explanation thereof will be omitted.

In addition to the configuration of the first embodiment, the tablet-inspecting device 7e of the fifth embodiment also includes a continuous drug packet detecting unit 42 for detecting the continuous drug packet 1. A detection signal from the continuous drug packet detecting unit 42 is input to the control unit 40.

The continuous drug packet detecting unit 42 is disposed more upstream of the conveyor path 8 than the imaging unit 10.

The control unit 40 gives, to the continuous drug packet-driving unit 9, i.e., the motor control unit 17, forward operation instructions for moving the continuous drug packet 1 from the upstream side to the downstream side of the conveyor path 8. The control unit 40 also gives, to the continuous drug packet-driving unit 9, i.e., the motor control unit 17, backward operation instructions for moving the continuous drug packet 1 from the downstream side to the upstream side of the conveyor path 8.

After the continuous drug packet 1 is thrown into the conveyor path 8, if the continuous drug packet detecting unit 42 detects a continuous drug packet 1, the control unit 40 gives the backward operation instructions to the motor control unit 17.

While the continuous drug packet detecting unit 42 detects a continuous drug packet 1 after the backward operation instructions, the control unit 40 keeps giving the backward operation instructions to the motor control unit 17.

When the continuous drug packet detecting unit 42 does not detect a continuous drug packet 1, the control unit 40 stops giving the backward operation instructions to the motor control unit 17. By stopping the backward operation instructions, the continuous drug packet 1 is disposed at a first initial position.

After the continuous drug packet 1 is disposed at a first initial position, the control unit 40 gives forward operation instructions to the motor control unit 17. The forward operation instructions from the control unit 40 is preset time or moving distance. By the forward operation instructions, the continuous drug packet 1 moves to a second initial position.

After the continuous drug packet 1 is disposed at the second initial position, the control unit 40 makes the imaging unit 10 take an image.

Next, an operation of the tablet-inspecting device 7e of the fifth embodiment will be described.

FIG. 18(*a*) is a sectional view showing a state where a continuous drug packet is thrown into the conveyor path by a manual operation in the drug inspecting apparatus of the embodiment, FIG. 18(*b*) is a sectional view showing a state where the drug continuous body is disposed at the first initial position in the drug inspecting apparatus, and FIG. 18(*c*) is a sectional view showing a state where the drug continuous body is disposed at the second initial position.

FIG. 19(*a*) is a plan view of a surface A-A in FIG. 18(*a*) as viewed from B, FIG. 19(*b*) is a plan view of a surface A-A in FIG. 18(*b*) as viewed from B, and FIG. 19(*c*) is a plan view of a surface A-A in FIG. 18(*c*) as viewed from B.

The continuous drug packet 1 is thrown into the conveyor path 8 by a manual operation.

In a initial state where an operation switch for starting an operation is operated, since there is no continuous drug packet 1, the continuous drug packet detecting unit 42 does not detect a continuous drug packet 1.

In this state, the continuous drug packet 1 is thrown into the conveyor path 8 by the manual operation. When the continuous drug packet 1 is thrown only to a position before the continuous drug packet detecting unit 42, the operation is not started.

FIGS. 18(*a*) and 19(*a*) show a state where a continuous drug packet 1 is thrown to a position exceeding the continuous drug packet detecting unit 42. The manual throwing operation may be carried out at a position where the continuous drug packet 1 exceeds the continuous drug packet detecting unit 42.

As shown in FIGS. 18(*a*) and 19(*a*), if a continuous drug packet 1 is thrown to a position exceeding the continuous drug packet detecting unit 42, the continuous drug packet detecting unit 42 detects the continuous drug packet 1.

If the continuous drug packet detecting unit 42 detects the continuous drug packet 1 after the continuous drug packet 1 is thrown into the conveyor path 8, a detection signal from the continuous drug packet detecting unit 42 is sent to the control unit 40. If the control unit 40 receives the detection signal from the continuous drug packet detecting unit 42, the control unit 40 gives the backward operation instructions to the motor control unit 17. The control unit 40 gives the operation instructions to the rotating body control unit 20B before the control unit 40 gives the operation instructions to the motor control unit 17, and the second rotating body 15 moves to press the continuous drug packet 1 from its upper surface.

The continuous drug packet 1 moves from the downstream side to the upstream side of the conveyor path 8 by this backward operation instructions.

While the continuous drug packet detecting unit 42 detects the continuous drug packet 1 after the backward operation instructions, the backward operation is continued.

That is, when a detection signal from the continuous drug packet detecting unit 42 is continued to be sent to the control unit 40, the backward operation instructions are continued.

When the continuous drug packet detecting unit 42 does not detect the continuous drug packet 1, the control unit 40 stops giving the backward operation instructions to the motor control unit 17. Therefore, the continuous drug packet 1 stops. This stop position is the first initial position F.

FIGS. 18(*b*) and 19(*b*) show a state where the continuous drug packet 1 is disposed at the first initial position F.

After the continuous drug packet 1 is disposed at the first initial position F, the control unit 40 gives the forward operation instructions to the motor control unit 17.

By the forward operation instructions, the continuous drug packet 1 moves from the upstream side to the downstream side of the conveyor path 8 at preset time or by a preset distance and then, the continuous drug packet 1 stops.

The forward operation from the control unit 40 is carried out at preset time or by a preset distance. By the forward operation, the continuous drug packet 1 moves to the second initial position. This stop position is the second initial position.

FIGS. 18(*c*) and 19(*c*) show a state where the continuous drug packet 1 is disposed at the second initial position.

After the continuous drug packet 1 is disposed at the first initial position F, the pressing operation of the rod unit 12, the reciprocating operation of the continuous drug packet 1 and the separating operation of the rod unit 12 described in the first embodiment are carried out and then, the continuous drug packet 1 moves to the second initial position.

The second initial position is a position where a top drug packet 3 of the continuous drug packet 1 is disposed at a region C where the imaging unit 10 takes an image of this drug packet 3.

After the continuous drug packet 1 is disposed at the second initial position, the image-taking operation is carried out by the imaging unit 10 and the tablet-inspecting operation is carried out by the tablet determining unit 11.

After the image-taking operation is carried out for the top drug packet 3 by the imaging unit 10, the following operations are carried out for a second drug packet 3. That is, the pressing operation of the rod unit 12, the reciprocating operation of the continuous drug packet 1, the separating operation of the rod unit 12, the sending operation and the image-taking operation of the drug packet 3.

For third and subsequent drug packets 3, the tablet-inspecting device 7e repeatedly carries out the pressing operation of the rod unit 12, the reciprocating operation of the continuous drug packet 1, the separating operation of the rod unit 12, the sending operation, the image-taking operation and the tablet-inspecting operation of the drug packet 3, thereby inspecting drugs in the respective drug packets 3 in the continuous drug packet 1.

After the continuous drug packet 1 is disposed at the first initial position F, the second tablet separating means 22 starts operating.

As described above, according to the fifth embodiment, it is possible to easily set up the continuous drug packet 1 at a predetermined position in the tablet-inspecting device 7e.

That is, in this embodiment, if the continuous drug packet detecting unit 42 detects that a continuous drug packet 1 is manually thrown (by human's hand), the continuous drug packet 1 is returned to the first initial position F. According to this, the continuous drug packet 1 can automatically be moved to the second initial position where the tablet-inspecting device 7e can start the inspecting operation.

In the fifth embodiment, to move the continuous drug packet 1 from the first initial position F to the second initial position, control for moving the continuous drug packet 1 by a desired constant amount (8 cm which is length of the drug packet 3 in the conveying direction). Alternatively, it is possible to employ such control that a mark is described on a drug packet 3 of the continuous drug packet 1, a detecting unit which recognizes the mark is provided in the tablet-inspecting device 7e, a position of the mark is detected, thereby controlling the moving amount. In this case, the continuous drug packet 1 can more precisely move from the first initial position F to the second initial position.

Although the fifth embodiment is described based on the configuration of the first embodiment, the fifth embodiment can similarly be applied to the configurations of other embodiments.

(Sixth Embodiment)

Next, a tablet-inspecting device in a sixth embodiment will be described.

First, a continuous drug packet used in the sixth embodiment will be described.

Figure 20:
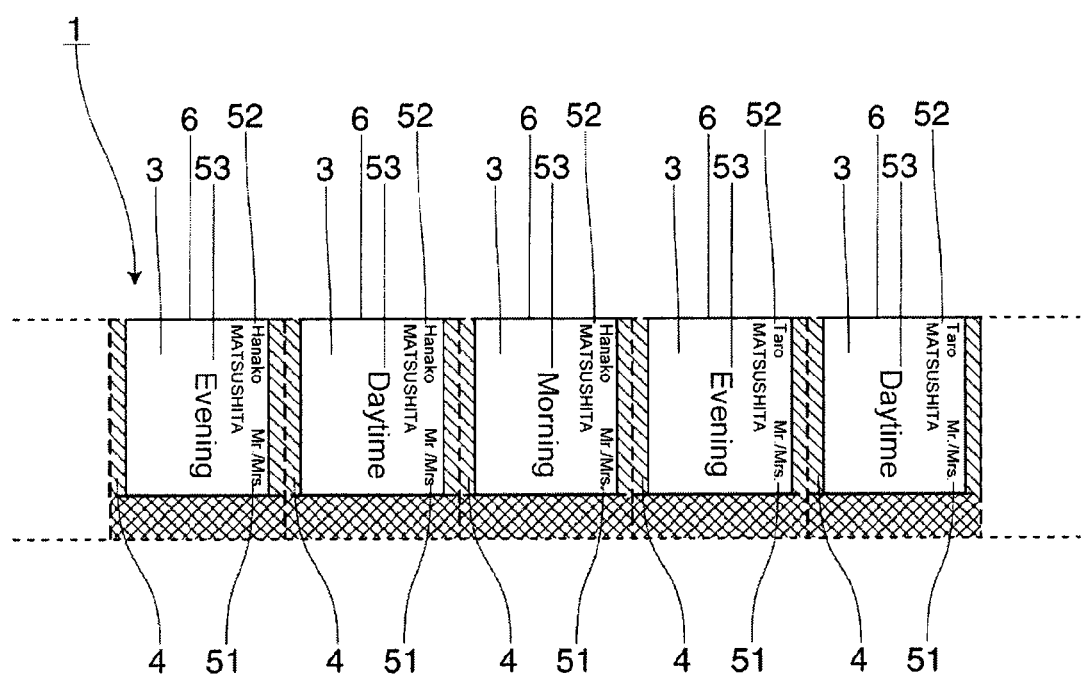
FIG. 20 is a bottom view of a continuous drug packet used in a tablet-inspecting device of the embodiments of the invention.

FIG. 20 is a bottom view of the continuous drug packet. A plan view of the continuous drug packet is as shown in FIG. 1.

As shown in FIG. 20, at least the other surface (lower surface) of a drug packet 3 is of see-through white translucent color, and characters 51 ("Mr./Mrs." in the drawing), characters 52 (names of patients ("Hanako MATSUSHITA", "Taro MATSUSHITA" in the drawing), and characters 53 ("Morning", "Daytime" and "Evening" in the drawing) are printed. Portions or all of the characters 51, 52 and 53 may be symbols.

Figure 21:
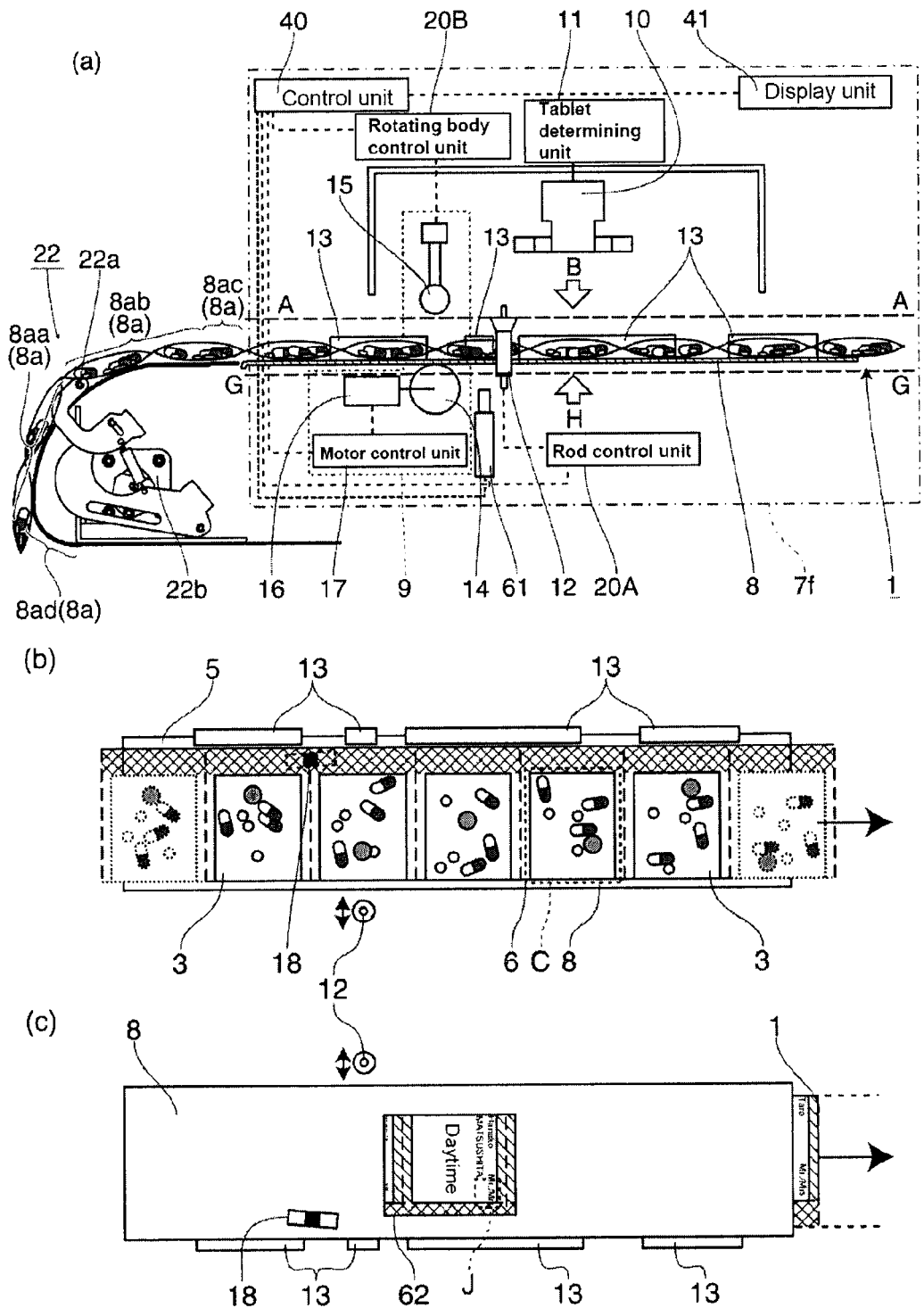
FIG. 21(a) is a partial sectional side view showing an outline configuration of a tablet-inspecting device in a sixth embodiment of the invention.
FIG. 21(b) is a plan view of a surface A-A in FIG. 21(a) as viewed from an arrow B (from above)
FIG. 21(c) is a bottom view of a surface G-G in FIG. 21(a) as viewed from an arrow H (from below)

FIG. 21(a) is a partial sectional side view showing an outline configuration of the tablet-inspecting device in the sixth embodiment, FIG. 21(b) is a plan view of a surface A-A in FIG. 21(a) as viewed from an arrow B (from above), and FIG. 21(c) is a bottom view of a surface G-G in FIG. 21(a) as viewed from an arrow H (from below). The same symbols are allocated to the same members as those of the above-described embodiment, and explanation thereof will be omitted.

According to the tablet-inspecting device 7f of the sixth embodiment, a drug packet detecting unit 61 is disposed on the conveyor path 8. A hole 62 is formed in a conveying surface of the conveyor path 8.

The drug packet detecting unit 61 is disposed on the conveyor path 8 at a location more downstream than the continuous drug packet-driving unit 9 and more upstream than the imaging unit 10.

The drug packet detecting unit 61 detects the characters 51 printed on every drug packet 3. A detection signal from the drug packet detecting unit 61 is sent to the control unit 40.

After the imaging unit 10 takes an image, the control unit 40 outputs a signal to the motor control unit 17 for making the motor control unit 17 carry out a first conveying operation. By the first conveying operation, the continuous drug packet 1 is moved by a first moving distance.

When the drug packet detecting unit 61 detects a symbol or the characters 51 during the first conveying operation, the control unit 40 then outputs a signal to the motor control unit 17 for making the motor control unit 17 carry out a second conveying operation. By the second conveying operation, the continuous drug packet 1 is moved from the detection position by a second moving distance.

When the drug packet detecting unit 61 is in a non-detected state where the drug packet detecting unit 61 can not detect a symbol or the characters 51, the control unit 40 outputs a signal to the motor control unit 17 for making the motor control unit 17 carry out a third conveying operation after predetermined time is elapsed after the first conveying operation is started. By the third conveying operation, the continuous drug packet 1 is moved by a third moving distance.

When the third conveying operation is carried out for predetermined continuous drug packets 3, the control unit 40 outputs a signal to the motor control unit 17 for making the motor control unit 17 stop the motor unit 16.

The hole 62 is formed in the conveying surface of the conveyor path 8 where the drug packet detecting unit 61 is located, and the drug packet detecting unit 61 detects, through the hole 62, the characters 51 described in the drug packet 3. A region where the drug packet detecting unit 61 detects the characters 51 is set to a region shown by a symbol J in FIG. 21(c).

Next, control of the sixth embodiment will be described using FIG. 22.

Figure 22:
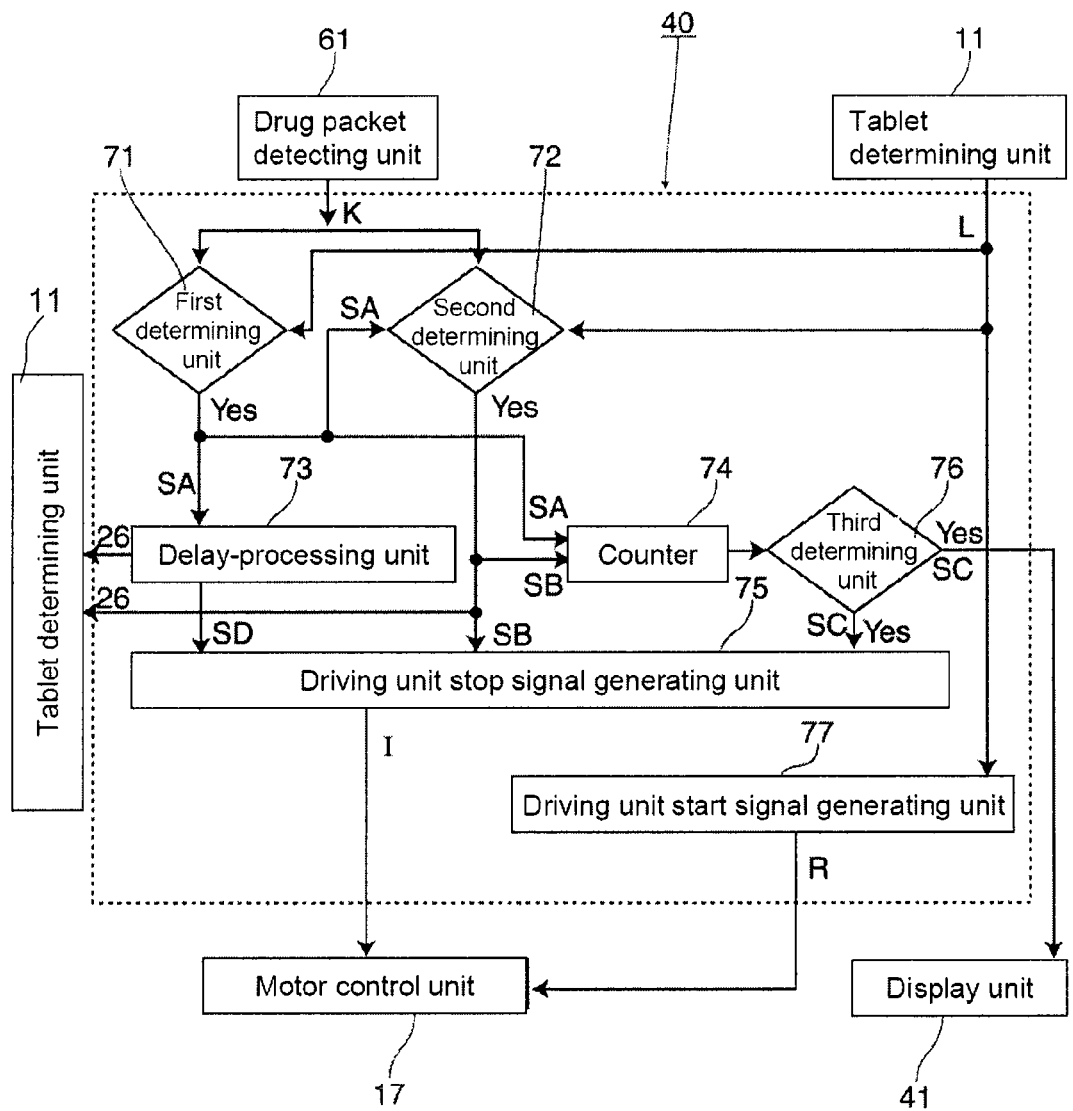
FIG. 22 is a block diagram showing control of the tablet-inspecting device of the embodiment.

FIG. 22 is a block diagram showing the control of the tablet-inspecting device of the sixth embodiment.

The drug packet detecting unit 61 inputs, to the control unit 40, a determining signal K including information concerning whether the characters 51 are detected. The determining signal K from the drug packet detecting unit 61 is input to a first determining unit 71 and a second determining unit 72.

The tablet determining unit 11 inputs a number of tablets determination-completion signal L to the control unit 40 after determination of the number of tablets of each of the drug packets 3 is completed.

The first determining unit 71 determines whether the drug packet detecting unit 61 recognized the characters 51 based on the determining signal K which is input after the number of tablets determination-completion signal L is received. If the first determining unit 71 determines that the drug packet detecting unit 61 recognized the characters 51, a signal SA is output to a delay-processing unit 73, a counter 74 and the second determining unit 72. After predetermined set time T1 is elapsed after the signal SA which was input from the first determining unit 71 is received, the delay-processing unit 73 outputs a signal SD to a driving unit stop signal generating unit 75.

The predetermined time T1 is time during which a second moving distance P (shown in FIG. 23) is realized. The predetermined time T1 is set from the second moving distance P and rotation speed of a first motor unit 16 (i.e., conveying speed of the continuous drug packet 1). For example, the second moving distance P was set to 3 cm, and the predetermined time T1 was set to 130 msec.

The signal SA which was input from the first determining unit 71 is received, the counter 74 resets a numeric value of the counter 74. This operation of the counter 74 will be described in detail later. If the second determining unit 72 receives the signal SA which was input from the first determining unit 71, a determining operation of the second determining unit 72 is stopped until the second determining unit 72 receives the number of tablets determination-completion signal L from the number of tablets determining unit 11.

After the second determining unit 72 receives, from the number of tablets determining unit 11, the number of tablets determination-completion signal L which is output after the determination of the number of tablets of each of the drug packet 3 is completed, if the second determining unit 72 does not receive the determining signal K even if predetermined set time T2 is elapsed (e.g., when the tablet-inspecting device is in the non-detected state where the characters 51 described in each of the drug packets 3 in the continuous drug packet 1 can not be detected), the second determining unit 72 outputs a signal SB to the driving unit stop signal generating unit 75 and the counter 74.

This predetermined time T2 is time required for moving through a distance of one drug packet 3, and the predetermined time T2 is calculated by dividing a length of the drug packet 3 by sending speed. For example, the predetermined time T2 was set to 500 msec.

After the signal SB which was input from the second determining unit 72 is received, the counter 74 increases a counter value of the counter 74 by one (plus one). An initial value of the counter 74 and a value after reset are zero. The counter 74 always output the counter value to a third determining unit 76.

The third determining unit 76 determines whether the counter value is equal to or greater than a preset numeric value based on the counter value which is input from the counter 74, and if the counter value is equal to or greater than the preset numeric value, the third determining unit 76 outputs a signal SC to the driving unit stop signal generating unit 75 and the display unit 41.

That is, when a case where the determining signal K with respect to the drug packet 3 is not received even if the predetermined time T2 is elapsed (when the tablet-inspecting device is in the non-detected state where the characters 51 described in each of the drug packets 3 can not be detected) continuously occurs predetermined times, the signal SC is output to the driving unit stop signal generating unit 75.

If the driving unit stop signal generating unit 75 receives any of the signals SD, SB and SC from the delay-processing unit 73, the second determining unit 72 or the third determining unit 76, the driving unit stop signal generating unit 75 outputs an operation stop signal I to the motor control unit 17. The motor control unit 17 which received the operation stop signal I stops the operation of the motor unit 16.

As described above, the control unit 40 receives the number of tablets determination-completion signal L which is output from the number of tablets determining unit 11 after the determination of the number of tablets of each of the drug packets 3 is completed, and this number of tablets determination-completion signal L is input to a driving unit start signal generating unit 77. If the driving unit start signal generating unit 77 receives the number of tablets determination-completion signal L, the driving unit start signal generating unit 77 outputs an operation start signal R to the motor control unit 17. The motor control unit 17 which received the operation start signal R starts the operation of the motor unit 16.

As described above, the third determining unit 76 determines whether the counter value is equal to or greater than the preset numeric value based on the counter value which is input from the counter 74, and if the counter value is equal to or greater than the preset numeric value, the third determining unit 76 outputs the signal SC to the driving unit stop signal generating unit 75 and the display unit 41. Thereafter, the driving unit stop signal generating unit 75 outputs the operation stop signal I to the motor control unit 17. According to this, the motor control unit 17 which received the operation stop signal I can stop the conveying operation of the continuous drug packet 1.

That is, in the sixth embodiment, when the third conveying operation is carried out for constant continuous drug packets 3, the continuous drug packet-driving unit 9 is stopped. According to this, when an abnormal state occurs, i.e., when a case where the non-detected state in which the characters 51 described in each of the drug packets 3 can not be detected occurs predetermined times, the tablet-inspecting device 7*f* can be stopped.

The display unit 41 to which this signal is input can display the fact that the non-detected state in which the characters 51 described in each of the drug packets 3 can not be detected occurs predetermined times. That is, in the sixth embodiment, it is possible to inform a user using the tablet-inspecting device 7*f* of the abnormal state that the non-detected state in which the characters 51 described in each of the drug packets 3 can not be detected occurs predetermined times.

In the sixth embodiment, if this predetermined time T2 is elapsed, the signal is immediately output to the driving unit stop signal generating unit 75. According to this, the operation stop signal I is output to the motor control unit 17 and thereafter, the motor control unit 17 which received the operation stop signal I stops the conveying operation of the continuous drug packet 1. Alternatively, it is also possible to employ such a configuration that after the predetermined time T2 is elapsed, the drug packet 3 is moved through a constant distance (corresponding to the third moving distance) and then, the signal is output tot he driving unit stop signal generating unit 75, thereby outputting the operation stop signal I to the motor control unit 17 and then, the motor control unit 17 which received the operation stop signal I stops the conveying operation of the continuous drug packet 1 (the third moving distance is set to zero).

It is ideal that the characters 51 can reliably be detected for all of drug packets 3, and the operation is carried out by this detection. In the actual case, however, a length of one continuous drug packet 1 is as long as about 7 m, a wrinkle of the continuous drug packet 1 or a floating of the drug packet 3 are generated due to this long length, and it is difficult to reliably detect the characters 51 of all of drug packets 3.

In out experience, detection errors of about 1% occur. When the detection errors occur, a "deviation" is generated between a drug packet 3 to be inspected and an inspected drug packet 3. Due to this "deviation", even if N-th drug packet 3 was inspected, it is determined that N−1-th drug packet 3 was inspected.

Thus, it is extremely important to provide an operation for a case where the characters 51 of a drug packet 3 could not be detected. Therefore, in the sixth embodiment, there is provided a conveying operation just in case a symbol or the characters 51 described on a drug packet 3 could not be detected.

First, a conveying operation carried out when a symbol described on the drug packet 3 in the continuous drug packet 1 could be detected will be described.

FIG. 23(*a*) is a bottom view showing a state immediately after completion of the counting operation of the number of tablets of in an N-th drug packet in a continuous drug packet in the tablet-inspecting device of the sixth embodiment, FIG. 23(*b*) is a bottom view showing a state where characters are recognized by the drug packet detecting unit in the first conveying operation in the tablet-inspecting device, and FIG. 23(*c*) is a bottom view showing a state where the state shown in FIG. 23(*b*) is moved by the second moving distance P. In the bottom views of FIG. 23 showing the surface G-G in FIG. 21 as viewed from H (from below), to make it easy to understand, the conveyor path 8 is omitted.

A conveying operation when the characters 51 could be detected includes a first conveying operation for moving a continuous drug packet 1 by a first moving distance M after the number of tablets in a drug packet 3 is counted, and a second conveying operation for moving the continuous drug packet 1 by a second moving distance P after the characters 51 described on the drug packet 3 are detected.

The first conveying operation will be described. As shown in FIG. 23, numbers N−2, N−1, N, N+1, N+2, N+3, . . . are allocated to drug packets 3 in this order from the downstream side (right side in the drawings) to the upstream side (left side in the drawings) of the conveyor path 8. These numbers correspond to the counting sequence of the number of tablets of the drug packets 3.

FIG. 23(a) shows the state immediately after the counting operation of the number of tablets of the N-th drug packet 3 in a continuous drug packet 1 is completed.

After the counting operation of the number of tablets of the N-th drug packet 3 is completed, the continuous drug packet 1 is moved by the first moving distance M from the upstream side (left side in FIG. 4) to the downstream side (right side in FIG. 4) by the first conveying operation.

That is, if the counting operation of the number of tablets of the N-th drug packet 3 is completed, the tablet determining unit 11 outputs, to the control unit 40, the number of tablets determination-completion signal L indicating that the the counting operation of the number of tablets of the N-th drug packet 3 is completed. Thereafter, the control unit 40 outputs the signal to the motor control unit 17, and moves the continuous drug packet 1 from the upstream side (left side in the drawings) to the downstream side (right side in the drawings) by the first moving distance M.

Here, since the size of each drug packet 3 in the longitudinal direction is 8 cm±0.3 cm, a margin is given to the first moving distance M and the distance M is set to 8+0.3+0.7 (margin)=9 cm.

Next, the second conveying operation will be described.

The drug packet detecting unit 61 inputs the determining signal K to the first determining unit 71 of the control unit 40. Then, if the first determining unit 71 determines that the drug packet detecting unit 61 recognized the characters 51, the first determining unit 71 outputs the signal SA to the delay-processing unit 73, the counter 74 and the second determining unit 72. Thereafter, if predetermined set time T1 is elapsed after the delay-processing unit 73 received the signal SA which was input from the first determining unit 71, the delay-processing unit 73 outputs the signal SD to the driving unit stop signal generating unit 75.

Therefore, the control unit 40 moves the continuous drug packet 1 by the second moving distance P from the upstream side (left side in the drawings) to the downstream side (right side in the drawings) by the motor control unit 17.

Here, the second moving distance P corresponds to a distance from a place (place shown in FIG. 23(b)) where the drug packet detecting unit 61 recognized the characters 51 during the first conveying operation to a place where an N+1-th drug packet 3 is disposed in the region C where the imaging unit 10 takes an image of the N+1-th drug packet 3.

For example, the second moving distance P is set to 3 cm from the place where the drug packet detecting unit 61 recognized the characters 51 during the first conveying operation. The second moving distance P is set to 3 cm, and the predetermined time T1 is set to 130 msec based on the second moving distance P and the rotation speed of the first motor unit 16 (i.e., conveying speed of the continuous drug packet 1).

After the second conveying operation, the continuous drug packet 1 moves from the upstream side to the downstream side of the conveyor path 8 so that the N+1-th drug packet 3 is located in the region C where the imaging unit 10 takes an image of the N+1-th drug packet 3 as shown in FIG. 23(c).

In the sixth embodiment, the operation for moving a drug packet 3 by the predetermined distance (second moving distance P) after characters 51 of the drug packet 3 are recognized. Alternatively, it is also possible to employ such a configuration that the drug packet detecting unit 61 is disposed such that a position where characters 51 of the drug packet 3 are recognized becomes the region C where the imaging unit 10 takes an image of the N+1-th drug packet 3, and when the characters 51 of the drug packet 3 are recognized, the continuous drug packet 1 is stopped. In this case, the predetermined distance (second moving distance P) becomes zero.

Next, a conveying operation carried out when a symbol described on a drug packet 3 in a continuous drug packet 1 could not be detected will be described.

FIG. 24(a) is a bottom view of a state immediately after completion of the counting operation of the number of tablets of the N-th drug packet in a continuous drug packet in the tablet-inspecting device of the sixth embodiment, and FIG. 24(b) is a bottom view showing a state of the tablet-inspecting device when the predetermined time T2 is elapsed after the first conveying operation is started.

The conveying operation carried out when the characters 51 could not be detected includes a first conveying operation for moving a continuous drug packet 1 by the first moving distance M after the number of tablets in a drug packet 3 is counted, and a third conveying operation for moving the continuous drug packet 1 by the third moving distance when the predetermined time T2 is elapsed after the first conveying operation is started.

The first conveying operation is the same as the conveying operation which is carried out when the characters 51 could be detected.

The third conveying operation will be described. As shown in FIG. 24(b) when the characters 51 are not recognized even after the predetermined time T2 is elapsed in the drug packet detecting unit 61 during the first conveying operation, it is determined that this situation is the non-detected state where the second determining unit 72 of the control unit 40 can not detect the characters 51 described on the drug packet 3, and the continuous drug packet 1 is moved by the third conveying operation by the third moving distance.

The predetermined time T2 is time required for moving a continuous drug packet 1 by a distance corresponding to a length of one drug packet 3 after the control unit 40 receives the number of tablets determination-completion signal L from the tablet determining unit 11 (after the number of tablets determination-completion signal L of the N-th drug packet 3 is received), and the predetermined time T2 is set to 500 msec for example. The third moving distance is set to zero as described above, and the third conveying operation for stopping the continuous drug packet 1 is carried out after the predetermined time T2 is elapsed.

Therefore, as shown in FIG. 24(a), after the counting operation of the number of tablets of the N-th drug packet 3 is completed, the first conveying operation for moving the continuous drug packet 1 from the upstream side (left side in the drawings) to the downstream side (right side in the drawings) is carried out. Then, after the predetermined time T2 is elapsed, the N+1-th drug packet 3 is moved by a distance Q as shown in FIG. 24(b). At this point, when the first determining unit 71 of the control unit 40 can not detect the characters 51 described on the N+1-th drug packet 3, and the second determining unit 72 of the control unit 40 immediately outputs the signal SB to the driving unit stop signal generating unit 75, thereby outputting the operation stop signal I to the motor control unit 17. Thereafter, the motor control unit 17 which received the operation stop signal I stops the operation of the motor unit 16 when 500 msec is elapsed after the first conveying operation is started.

After this third conveying operation, the continuous drug packet 1 moves from the upstream side to the downstream side of the conveyor path 8 so that the N+1-th drug packet 3 comes to the region C where the imaging unit 10 takes an image of the N+1-th drug packet 3.

In the sixth embodiment, the second conveying operation is carried out by recognizing the characters 51 of a drug packet 3, but other characters 52, 53 or other symbol may be recognized.

According to the sixth embodiment, it is possible to precisely move drug packets 3 in a continuous drug packet 1 to the region C where the imaging unit 10 takes images of the drug packets.

That is, in the sixth embodiment, the characters 51 described on a drug packet 3 in a continuous drug packet 1 are detected and based on this detection, and the drug packet 3 in the continuous drug packet 1 can be moved to the region C where the imaging unit 10 takes an image of the drug packet 3.

According to the sixth embodiment, when the tablet-inspecting device is in the non-detected state where the drug packet detecting unit 61 cannot detect the characters 51 described on a drug packet 3 during the first conveying operation, the third conveying operation for moving a continuous drug packet 1 by the second moving distance P is carried out when the predetermined time T2 is elapsed after the first conveying operation is started. According to this, even if a detection error of the drug packet detecting unit 61 occurs due to a stain or a wrinkle on the drug packet 3, it is possible to move a drug packet 3 to the region C where the number of tablets can be counted by carrying the time control. Therefore, it is possible to reduce variation in a moving distance caused by size variation of drug packets 3 in a continuous drug packet 1, and it is possible to reliably move a drug packet 3 to the region C where the imaging unit 10 takes an image of the drug packet 3.

After the moving operation of one drug packet 3 to the region C is completed, the pressing operation of the rod unit 12, the reciprocating operation of a continuous drug packet 1 and the separating operation of the rod unit 12 are carried out.

(Seventh Embodiment)

A tablet-inspecting device in a seventh embodiment of the invention will be described.

FIG. 25(a) is a partial sectional side view showing an outline configuration of the tablet-inspecting device in the seventh embodiment, and FIG. 25(b) is a plan view of a surface A-A in FIG. 25(a) as viewed from an arrow B (from above).

The tablet-inspecting device 7g of the seventh embodiment includes a recess forming means 80 for forming a recess 90 in a continuous drug packet 1. The recess forming means 80 is disposed more downstream of the conveyor path 8 than the imaging unit 10. The recess forming means 80 is composed of a pressing body 81 and a pedestal 82.

A hole (not shown) is formed in the conveyor path 8 located between the pressing body 81 and the pedestal 82, and the pressing body 81 and the pedestal 82 can abut against each other in the hole. The pressing body 81 and the pedestal 82 sandwich a continuous drug packet 1 from its upper and lower surfaces, thereby forming form the recess 90 in the continuous drug packet 1.

It is preferable that the recess 90 is formed in the clamped portion 5. Therefore, the recess forming means 80 is disposed on the clamped portion 5 of the continuous drug packet 1.

The pressing body 81 carries out a vertically moving operation by a pressing body control unit 20C. The pressing body control unit 20C operates the pressing body 81 by operation instructions from the control unit 40.

The control unit 40 forms the recess 90 in the continuous drug packet 1 based on a inspecting result of the tablet determining unit 11.

Next, a recess forming operation of the tablet-inspecting device of the seventh embodiment will be described.

The recess forming operation is carried out after the counting operation of the number of tablets is carried out and the continuous drug packet 1 is moved. After the pressing operation of the rod unit 12, the recess forming operation is not carried out until the reciprocating operation of the continuous drug packet 1 and the separating operation of the rod unit 12 are carried out.

To count the number of tablets in a drug packet 3, the imaging unit 10 takes an image of tablets 2 of an N-th drug packet 3. The shoot image data is taken into the tablet determining unit 11 and then, the image data is image-processed and the number of tablets 2 is counted. From a result of the counting operation of the number of tablets, it is determined whether the number is a desired number, and this result is output to the control unit 40.

After the counting operation of the number of tablets of the N-th drug packet 3 in the continuous drug packet 1 is completed, the control unit 40 outputs an operation signal to the motor control unit 17 so that the continuous drug packet 1 moves from the upstream side (left side in the drawings) to the downstream side (right side in the drawings) by a distance of a length of one drug packet 3.

By this operation, the N-th drug packet 3 moves to the recess forming means 80.

The control unit 40 outputs operation instructions to the pressing body control unit 20C based an a result of the counting operation of the number of tablets of the N-th drug packet 3 which moved to the recess forming means 80. By the operation instructions, the recess 90 is formed in the clamped portion 5 of the drug packet 3 of the continuous drug packet 1.

In the seventh embodiment, if a result of the counting operation of the number of tablets of a drug packet 3 is no good (if tablets of desired number are not included in the N-th drug packet 3), the recess 90 is formed in the clamped portion 5 of the drug packet 3 of the continuous drug packet 1.

That is, the control unit 40 determines whether a result of the counting operation of the number of tablets of the N-th drug packet 3 is no good, and only when the result is no good, the control unit 40 outputs the operation signal to the pressing body control unit 20C. By the pressing body control unit 20C which received the operation signal, the pressing body 81 and the pedestal 82 sandwich the clamped portion 5 of the continuous drug packet 1, and the recess 90 is formed in the clamped portion 5 of the continuous drug packet 1.

Figure 25:
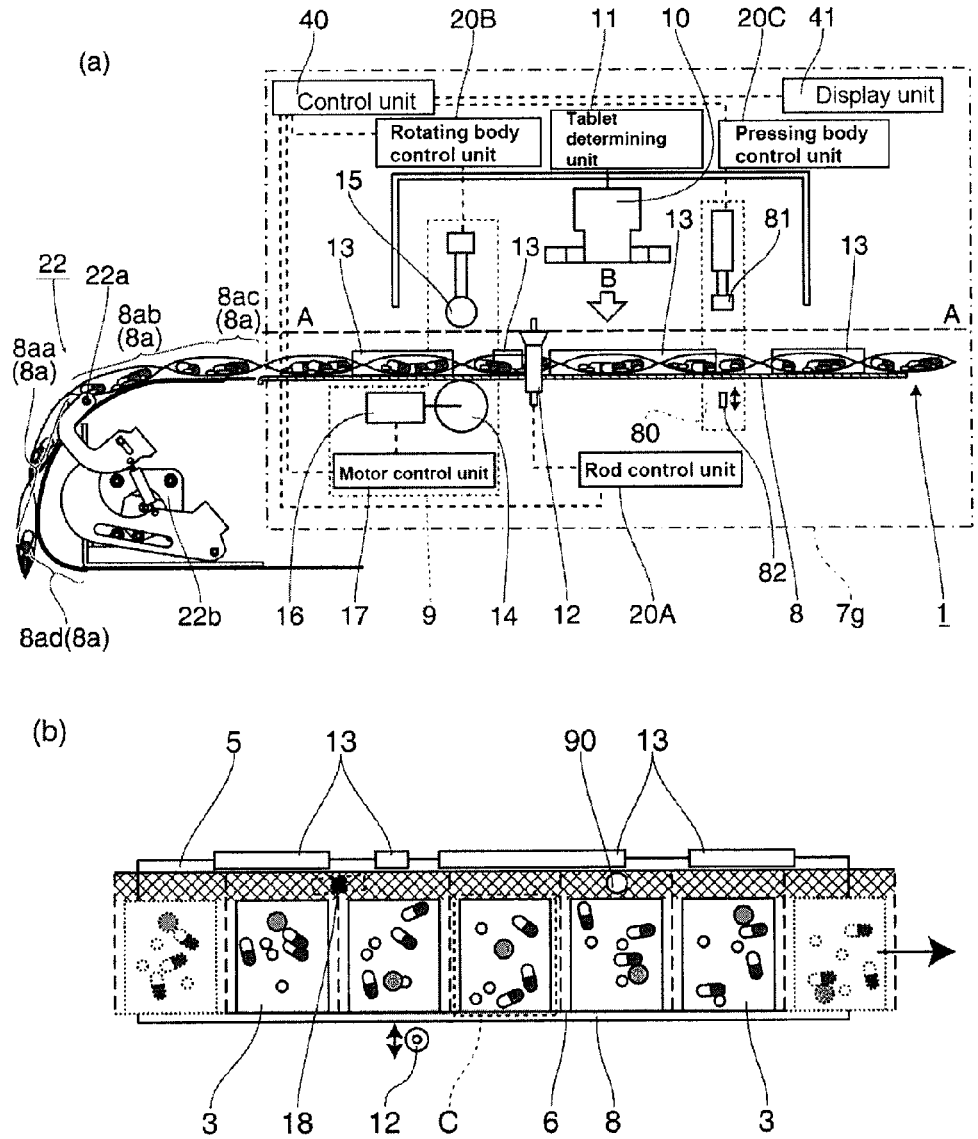
FIG. 25(a) is a partial sectional side view showing an outline configuration of a tablet-inspecting device in a seventh embodiment of the invention.
FIG. 25(b) is a plan view of a surface A-A in FIG. 25(a) as viewed from an arrow B (from above).

The recess 90 is "circular" as shown in FIG. 25, but the recess 90 may be formed into a triangle shape, a square shape or a star shape.

In the seventh embodiment, the recess 90 is formed in the clamped portion 5 of the drug packet 3 of the continuous drug packet 1 only when the result of the counting operation of the number of tablets of the drug packet 3 is no good, but if two kinds heater bars having different shapes are prepared, two kinds of recesses 90 (one is for good result and the other is for no good result) can be formed not only when the result of the counting operation of the number of tablets of the drug packet 3 is no good. If a plurality of recess forming means 80 having different shapes are prepared, a plurality of states of a drug packet 3 can be displayed based on a result of the counting operation of the number of tablets of the drug packet 3.

The drive-assisting unit 24 described in the second embodiment can be applied to the fourth to the seventh embodiments. The third tablet separating means 30 described in the third embodiment can be applied instead of the second tablet separating means 22 in the fourth to the seventh embodiments. The first rotating body 14a and the second rotating body 15a described in the fourth embodiment can be applied to the first rotating body 14, the second rotating body 15, the third rotating body 24a and the fourth rotating body 24b of the fifth to the seventh embodiments. The continuous drug packet detecting unit 42 described in the fifth embodiment can be applied to the sixth and seventh embodiments. The drug packet detecting unit 61 described in the sixth embodiment can be applied to the seventh embodiment.

INDUSTRIAL APPLICABILITY

Since the present invention can provide the tablet-inspecting device capable of stably counting the number of drugs, the invention is useful for a tablet-inspecting device of a drug packet in a hospital.

The invention claimed is:

1. A tablet-inspecting device comprising:
a conveyor path on which a continuous drug packet composed of a plurality of drug packets arranged in a row moves,
a continuous drug packet-driving unit for moving the continuous drug packet from an upstream side to a downstream side of the conveyor path,
an imaging unit for taking an image of tablets included in the drug packet, and
a tablet determining unit for inspecting the tablets based on the image of the tablets taken by the imaging unit, wherein
the continuous drug packet-driving unit is disposed more upstream of the conveyor path than the imaging unit, the tablet-inspecting device further comprises:
a rod unit which is pressed against a side portion of the drug packet is disposed between the continuous drug packet-driving unit and the imaging unit,
a rod control unit for operating the rod unit, and
a control unit for giving operation instructions to the continuous drug packet-driving unit and the rod control unit,
wherein the control unit gives, to the continuous drug packet-driving unit,
operation instructions to move the continuous drug packet from the upstream side to the downstream side of the conveyor path, and
reciprocating operation instructions to alternately move the continuous drug packet to the upstream side and the downstream side of the conveyor path, and wherein;
the control unit gives, to the rod control unit, rod unit-pressing operation instructions to press the rod unit against the side portion of the drug packet, and
when the control unit gives the reciprocating operation instructions to the continuous drug packet-driving unit, the control unit has given the rod unit-pressing operation instructions to the rod control unit.

2. The tablet-inspecting device according to claim 1, wherein an introduction path is provided upstream of the conveyor path,
tablet separating means is disposed on the introduction path,
the tablet separating means includes:
a rod crossing the introduction path, and
a driving unit for alternately moving the rod to an upstream side and a downstream side of the introduction path,
a portion of the introduction path located more upstream than a moving range of the rod is set lower than a portion of the introduction path located in the moving range of the rod, and
the rod abuts against a lower surface of the continuous drug packet.

3. The tablet-inspecting device according to claim 1, wherein tablet separating means is disposed more upstream than an upstream end of the conveyor path,
the tablet separating means includes:
vibrating means disposed above the conveyor path, and
a vibration space provided between the vibrating means and the upstream end of the conveyor path, and
a length of the vibration space from the vibrating means to the conveyor path is set longer than a length of the drug packet in a conveying direction.

4. The tablet-inspecting device according to claim 1, wherein a clamped portion formed by superposing powder wrapping paper sheets on each other and clamping the powder wrapping paper sheets is formed on one of sides of the continuous drug packet in its longitudinal direction,
a folded back portion formed by folding back the powder wrapping paper sheets is formed on an other side of the continuous drug packet in the longitudinal direction,
the continuous drug packet is composed of:
a first rotating body disposed on a lower portion of the conveyor path,
a second rotating body disposed on an upper portion of the conveyor path, and
a motor unit connected to the first rotating body, and
the first rotating body and the second rotating body are in contact with the clamped portion.

5. The tablet-inspecting device according to claim 4, wherein a guide is provided on at least one side surface of the conveyor path, and
a rotation shaft of at least one of the first rotating body and the second rotating body is oriented to such a direction that discharging directions of the first rotating body and the second rotating body approach the guide.

6. The tablet-inspecting device according to claim 1, wherein the rod unit includes a columnar first rotating unit, and
the first rotating unit comes into contact with a side surface of the drug packet, thereby rotating the first rotating unit in tandem with a reciprocating operation of the continuous drug packet.

7. The tablet-inspecting device according to claim 6, wherein the rod unit includes a truncated conical second rotating unit at a location higher than the first rotating unit, and
the second rotating unit rotates in tandem with the reciprocating operation of the continuous drug packet.

8. The tablet-inspecting device according to claim 3, wherein a guide path extending from an upstream side of the tablet separating means toward the tablet separating means is upwardly tilted.

9. The tablet-inspecting device according to claim 8, wherein the upstream end of the conveyor path is downwardly tilted.

10. The tablet-inspecting device according to claim 3, wherein the vibrating means includes:
a roller which rotates in a travelling direction of the continuous drug packet, and
a vibrating motor for vibrating the roller, wherein
the continuous drug packet is placed on an outer surface of the roller.

11. The tablet-inspecting device according to claim 10, wherein the continuous drug packet is supplied toward the roller from a location on an upstream side of the roller and lower than the roller.

12. The tablet-inspecting device according to claim 4, wherein the first rotating body is made of rubber, and the second rotating body is made of plastic.

13. The tablet-inspecting device according to claim 1, wherein a continuous drug packet detecting unit for detecting the continuous drug packet is disposed more upstream of the conveyor path than the imaging unit,
the control unit gives, to the continuous drug packet-driving unit,
forward operation instructions to move the continuous drug packet from the upstream side to the downstream side of the conveyor path, and
backward operation instructions to move the continuous drug packet from the downstream side to the upstream side of the conveyor path,
wherein if the continuous drug packet detecting unit detects the continuous drug packet after the continuous drug packet is thrown, the control unit gives the backward operation instructions,
wherein while the continuous drug packet detecting unit is detecting the continuous drug packet after the backward operation instructions, the control unit keeps giving the backward operation instructions,
wherein when the continuous drug packet detecting unit does not detect the continuous drug packet, the control unit stops giving the backward operation instructions, thereby disposing the continuous drug packet at a first initial position,
wherein after the continuous drug packet is disposed at the first initial position, the control unit gives the forward operation instructions, thereby moving the continuous drug packet to a second initial position, and
after the continuous drug packet is disposed at the second initial position, the control unit makes the imaging unit take an image.

14. The tablet-inspecting device according to claim 1, wherein a drug packet detecting unit for detecting a symbol or a character printed on each of the drug packets is disposed on the conveyor path.

15. The tablet-inspecting device according to claim 14, wherein the control unit carries out a first conveying operation for moving the continuous drug packet by a first moving distance after the imaging unit takes an image, and
if the drug packet detecting unit detects the symbol or the character during the first conveying operation, the control unit carries out a second conveying operation for moving the continuous drug packet by a second moving distance after the detection.

16. The tablet-inspecting device according to claim 15, wherein the second moving distance is set smaller than the first moving distance.

17. The tablet-inspecting device according to claim 15, wherein if the tablet-inspecting device is in a non-detected state where the drug packet detecting unit can not detect the symbol or the character during the first conveying operation, the control unit carried out a third conveying operation for moving the continuous drug packet by a third moving distance when predetermined time is elapsed after the first conveying operation is started.

18. The tablet-inspecting device according to claim 17, wherein when the third conveying operation is carried out for predetermined continuous some of the drug packets, the control unit stops the continuous drug packet-driving unit.

19. The tablet-inspecting device according to claim 1, further comprising a recess forming means for forming a recess in the continuous drug packet, wherein
the control unit makes the recess forming means form the recess in the continuous drug packet based on a result of a inspecting operation carried out by the tablet determining unit.

20. The tablet-inspecting device according to claim 19, wherein a clamped portion formed by superposing powder wrapping paper sheets on each other and clamping the powder wrapping paper sheets is formed on one of sides of the continuous drug packet in its longitudinal direction,
a folded back portion formed by folding back the powder wrapping paper sheets is formed on an other side of the continuous drug packet in the longitudinal direction, and
the recess is formed in the clamped portion.

21. A drug packet inspected using the tablet-inspecting device according to claim 19, wherein the recess is formed in the drug packet.

22. A continuous drug packet inspected using the tablet-inspecting device according to claim 19, wherein the recess is formed in any of the drug packets.

23. A tablet-inspecting device comprising:
a conveyor path on which a continuous drug packet composed of a plurality of drug packets arranged in a row moves,
a continuous drug packet-driving unit for moving the continuous drug packet from an upstream side to a downstream side of the conveyor path,
an imaging unit for taking an image of tablets included in the drug packet, and
a tablet determining unit for inspecting the tablets based on the image of the tablets taken by the imaging unit, wherein;
an introduction path is provided upstream of the conveyor path,
a tablet separating means is disposed on the introduction path,
wherein the tablet separating means includes;
a rod crossing the introduction path, and
a driving unit for alternately moving the rod to an upstream side and a downstream side of the introduction path,
wherein a portion of the introduction path that is located more upstream than a moving range of the rod is set lower than a portion of the introduction path located in the moving range of the rod, and
the rod abuts against a lower surface of the continuous drug packet.

* * * * *